United States Patent [19]
Matsuda et al.

[11] Patent Number: 5,763,504
[45] Date of Patent: Jun. 9, 1998

[54] PHOTCURABLE GLYCOSAMINOGLYCAN DERIVATIVES, CROSSLINKED GLYCOSAMINOGLYCANS AND METHOD OF PRODUCTION THEREOF

[75] Inventors: Takehisa Matsuda, Osaka, Japan; Minoo J. Moghaddam, Marsfield, Australia; Katsukiyo Sakurai, Tokyo, Japan

[73] Assignee: Seikagaku Kogyo Kabushiki Kaisha(Seikagaku Corporation), Tokyo, Japan

[21] Appl. No.: 476,236

[22] Filed: Jun. 7, 1995

Related U.S. Application Data

[62] Division of Ser. No. 13,799, Feb. 5, 1993, abandoned.

[30]     Foreign Application Priority Data

| Feb. 5, 1992 | [JP] | Japan | 4-47744 |
| Jul. 8, 1992 | [JP] | Japan | 4-203209 |
| Dec. 21, 1992 | [JP] | Japan | 4-355441 |

[51] Int. Cl.$^6$ .............. C08G 64/00; C08G 69/08; C08G 73/10; A61K 9/50
[52] U.S. Cl. .............. 522/87; 522/88; 523/105; 527/200; 527/201; 527/312; 527/313; 527/314; 527/315; 514/8; 424/447; 424/423; 424/499
[58] Field of Search .............. 522/74, 78, 79, 522/84, 86, 87, 88; 523/105, 111; 527/312, 313, 314, 315, 200, 201

[56]         References Cited

U.S. PATENT DOCUMENTS

| 3,920,618 | 11/1975 | Ichimura et al. | 522/149 |
| 3,960,685 | 6/1976 | Sano et al. | 204/159.12 |
| 4,141,973 | 2/1979 | Balazs | 424/180 |
| 4,331,697 | 5/1982 | Kudo et al. | 427/2 |
| 4,716,154 | 12/1987 | Malson et al. | 514/54 |
| 4,716,224 | 12/1987 | Sakurai et al. | 514/54 |
| 4,722,906 | 2/1988 | Guire | 436/501 |
| 4,745,098 | 5/1988 | Michaeli | 514/2 |
| 4,863,907 | 9/1989 | Sakurai et al. | 514/56 |
| 4,886,787 | 12/1989 | De Belder et al. | 514/57 |
| 4,973,493 | 11/1990 | Guire | 427/2 |
| 4,979,959 | 12/1990 | Guire | 623/66 |
| 5,002,582 | 3/1991 | Guire et al. | 623/66 |
| 5,128,326 | 7/1992 | Balazs et al. | 514/54 |
| 5,143,724 | 9/1992 | Leshchiner et al. | 424/78.08 |
| 5,190,759 | 3/1993 | Lindblad et al. | 424/423 |
| 5,217,492 | 6/1993 | Guire et al. | 623/11 |
| 5,246,698 | 9/1993 | Leshchiner et al. | 424/78.08 |
| 5,356,883 | 10/1994 | Kuo et al. | 514/54 |
| 5,358,973 | 10/1994 | Lindblad et al. | 574/777 |

FOREIGN PATENT DOCUMENTS

| A3912122 | 10/1990 | Germany . | |
| 0128482 | 10/1979 | Japan | 522/88 |
| A57-89751 | 6/1982 | Japan . | |
| A57-89752 | 6/1982 | Japan . | |
| B60-16260 | 4/1985 | Japan . | |
| B0139569 | 8/1989 | Japan . | |
| B0235750 | 8/1990 | Japan . | |
| A03264523 | 11/1991 | Japan . | |

OTHER PUBLICATIONS

Patent Abstract of Japan vol. 5, No. 106 (C-062) 10 Jul. 1981 & JP-A-56 047 439 (Japan Synthetic Rubber Co. Ltd) 30 Apr. 1981.

Shimomura et al, "Photochemical Reaction of Stilbazole Amphiphile in Cast Oriented Film", Dept Biotech., Tokyo U. 1984 Japan (Abstract).

Asaio Journal, 1992, "Photoinduced Prevention of Tissue Adhesion", by T. Matsuda, M.J. Moghaddam, H. Miwa, K. Sakurai and F. Iida.

*Primary Examiner*—Susan W. Berman
*Attorney, Agent, or Firm*—Sughrue, Mion, Zinn, Macpeak & Seas

[57]            ABSTRACT

Photocurable glycosaminoglycan (GAG) derivatives and crosslinked glycosaminoglycans, which are highly safe and biocompatible, a method of preparing such photocurable GAG derivatives readily moldable by casting using a solvent when desired, by which method unreacted substances causative of adverse effects can be readily eliminated, and a method of producing the crosslinked GAGs and medical materials based on the photocurable GAG derivatives or crosslinked GAGs are provided. The photocurable GAG derivatives comprise a glycosaminoglycan and a photoreactive compound bound thereto and can be produced, for example, by subjecting hydroxyl or carboxyl groups of the glycosaminoglycan to esterification reaction or amidation reaction, respectively, with the photoreactive compound. The crosslinked GAGs are derived from the photocurable GAG derivatives by intermolecular crosslinking of the photoreactive compound bound thereto.

13 Claims, 20 Drawing Sheets

○ ADVANCING CONTACT ANGLE
● RECEDING CONTACT ANGLE

DS=0.5

DS=0.87

DS=1.29

DS=2.43

— ADVANCING CONTACT ANGLE
--- RECEDING CONTACT ANGLE

PHOTCURABLE GLYCOSAMINOGLYCAN DERIVATIVES, CROSSLINKED GLYCOSAMINOGLYCANS AND METHOD OF PRODUCTION THEREOF

This is a divisional of application Ser. No. 08/013,799 filed Feb. 5, 1993, now abandoned.

FIELD OF THE INVENTION

The present invention relates to photocurable glycosaminoglycan derivatives each prepared by chemically binding a photoreactive compound to a glycosaminoglycan (hereinafter sometimes referred to as "GAG" for short), and crosslinked glycosaminoglycans having a three-dimensional network structure as obtained by subjecting said derivatives to photoreaction for dimerization of the photoreactive compound, to methods of preparing them and, further, to satisfactorily biocompatible materials for medical use which comprise the same.

BACKGROUND OF THE INVENTION

Photocurable resins comprising hydrophobic polymer systems to be subjected to photodimerization for crosslinking have so far been used in lithography, paints and printing, among others. On the contrary, there are few examples known where hydrophilic polymers are photocrosslinked.

On the other hand, attempts have been made to crosslink GAGs, which are typical hydrophilic polymers, by means of aldehydes, epoxy compounds, divinyl sulfone compounds and the like for prolonging the actions of GAGs in vivo or for preparing materials for medical use in the form of films or powders, for example for preventing tissue adhesion. However, since GAGs are macromolecules, the crosslinked GAG derivatives formed are still higher in molecular weight and this fact makes it difficult to completely remove unreacted materials and/or catalysts from the crosslinked GAG derivatives. Thus, when administered to or implanted into living bodies, said derivatives may frequently produce adverse effects, so that they are not suited for practical use. In addition, crosslinked GAG derivatives occur as gels or solids and therefore are difficult to mold after crosslinking, hence not suited for practical use. Furthermore, as for their use as carriers in sustained or controlled release drug preparations (JP-A-62-129226 corresponding to U.S. Pat. No. 5,128,326; the term "JP-A" used herein means an unexamined published Japanese patent application), sustained release of active ingredients can be attained only by taking advantage of the viscous property of crosslinked GAG derivatives and this disadvantage renders them unsuited for practical use. Thus, such methods and crosslinked GAG derivatives can hardly control the rate of release of drugs.

It is also known that photosensitive materials prepared by esterifying hydroxyl groups of microorganism or plant derived polysaccharides such as pullulan, amylose and mannan with cinnamoyl groups which are photodimerizable functional groups are usable as adsorbents, enzyme carriers or carriers for chromatography or in producing PS plates or photoresists or for other applications [JP-B-56-14969 corresponding to U.S. Pat. No. 3,960,685 (the term "JP-B" used herein means an examined published Japanese patent application), JP-A-60-219202].

However, the photosensitive materials mentioned above have a problem in securing safety, can hardly control cell adhesion and are poor in biocompatibility in humans and, therefore, they are not suited for use as medical materials to be directly applied to living bodies, in particular artificial organs, medical products to be used for covering wounds or in surgery, carriers in pharmaceutical preparations, or other materials to be used for some or other medical treatment.

SUMMARY OF THE INVENTION

Accordingly, it is an object of the present invention to provide photocurable glycosaminoglycan derivatives and crosslinked glycosaminoglycans derived therefrom, which are highly safe and biocompatible.

Another object of the invention is to provide a method of preparing photocurable glycosaminoglycan derivatives readily moldable, when desired, for example by casting using a solvent, by which method unreacted substances causative of adverse effects, among others, can be readily eliminated, and a method of producing crosslinked GAGs therefrom.

A third object of the invention is to provide materials for medical use which are based on said photocurable GAG derivatives or crosslinked GAGs and are widely applicable for various purposes.

A fourth object of the invention is to provide nonadhesive materials comprising a crosslinked glycosaminoglycan which is not adherent to tissues but is biodegradable in accordance with the rate of wound healing and whose mechanical strength can be readily adjusted according to the mechanical stress at the site of application, and nonadhesive materials comprising a photocurable glycosaminoglycan derivative readily convertible to a crosslinked glycosaminoglycan upon irradiation with light in vivo.

A fifth object of the invention is to provide materials or preparations for realizing controlled drug release which comprise a crosslinked glycosaminoglycan and allow drug release at a rate suited for the drug included, entrapped or embedded therein and for the purpose of the drug application, as well as materials for realizing controlled drug release which comprise a photocurable glycosaminoglycan and are useful as carriers in the materials or preparations mentioned above or as starting materials therefor.

The present invention provides a photocurable glycosaminoglycan derivative (hereinafter sometimes referred to as "photocurable GAG"E for short) which comprises a glycosaminoglycan and a photoreactive compound bound thereto, and a crosslinked glycosaminoglycan (hereinafter sometimes referred to as "crosslinked GAG" for short) prepared by subjecting said photocurable GAG to crosslinking reaction of said photoreactive compound. Said photocurable GAG can preferably be produced by subjecting hydroxyl or carboxyl groups of the glycosaminoglycan to esterification reaction with the photoreactive compound, by activating carboxyl groups of the glycosaminoglycan and subjecting the activated carboxyl groups to amidation reaction with the photoreactive compound, or by subjecting carboxyl groups of the glycosaminoglycan to amidation reaction with the photoreactive compound in the presence of a condensing agent. The crosslinked glycosaminoglycan can be produced by irradiating the photocurable GAG with light to thereby cause the crosslinking reaction of the photoreactive compound moieties one with another. Materials based on said crosslinked GAG are suited for medical use. The photocurable GAG, which gives said crosslinked GAG, can also serve as a material for medical use.

DETAILED DESCRIPTION OF THE INVENTION

Figure 1:
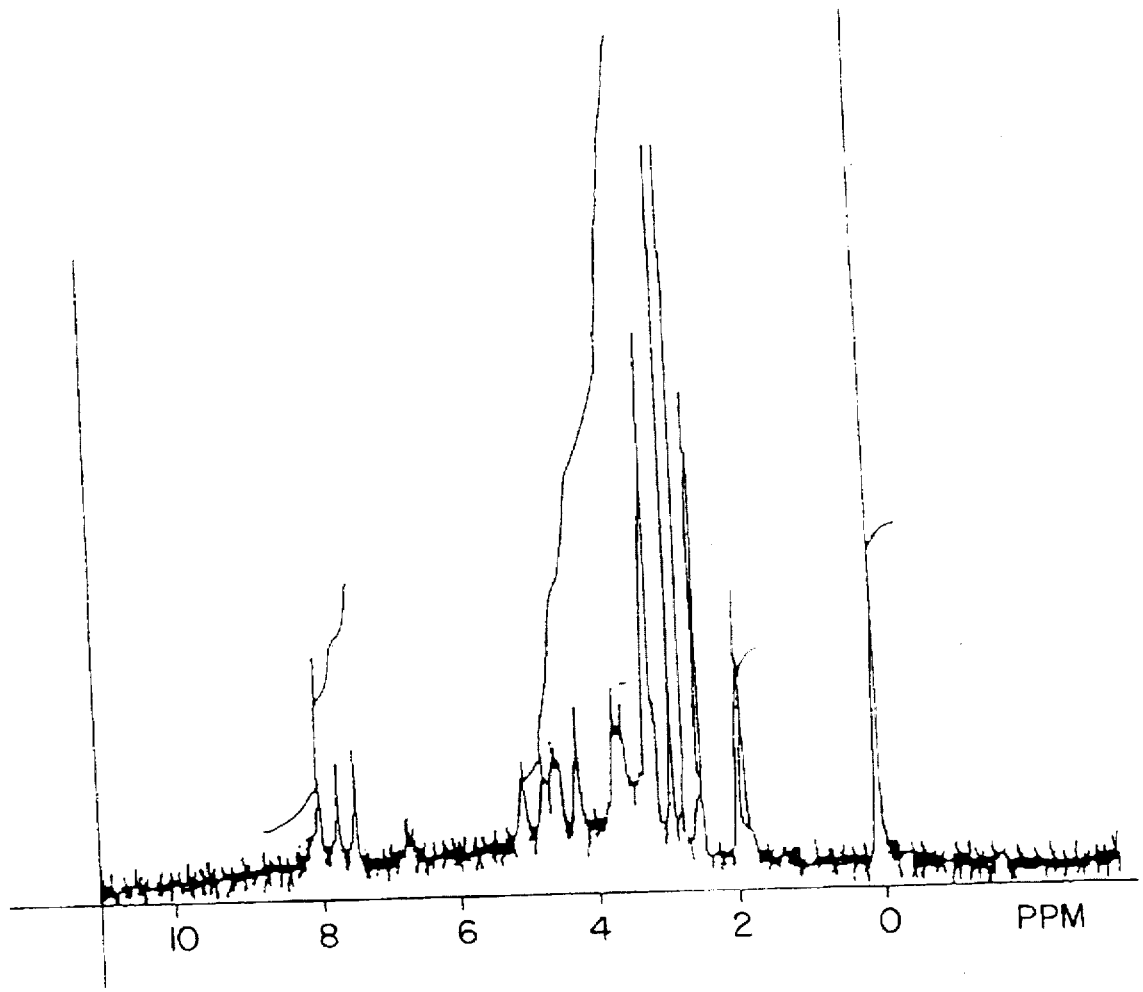
FIG. 1 shows the $^1$H-NMR spectrum used for bound cinnamic acid quantity determination in Example 1.

The term "materials for medical use" is used herein to include, among others, materials for constructing medical devices to be used for diagnostic on therapeutic purposes or artificial organs (artificial blood vessel, artificial heart, artificial skin, etc.), materials constituting wound coverings, prosthetics, nonadhesive materials or devices for controlled drug release, and artificial extracellular matrices or artifical basement membranes which are useful for the adhesion and multiplication of endothelial cells, epithelial cells and smooth muscle cells in the formation of hybrid artificial organs.

The photocurable GAG of this invention preferably has a partial structure representable by one of the formulas [1] to

[5] given below and, when subjected to photoreaction, gives a crosslinked GAG. Below each of said formulas, the corresponding mode of reaction is given, wherein gag means a partial structure of any glycosaminoglycan, $R^1$ is a photoreactive group (i.e. a group containing at least a vinylene group), and $R^1$—COOH, $R^1$—$NH_2$ and $R^1$—OH each is a photoreactive compound.

[A] gag-O—(CO—$R^1$) [1]

gag-OH+$R^1$—COOH→ester bonding→[1]

[B] gag-CO—(NH—$R^1$) [2]

gag-COOH+$R^1$—$NH_2$ →amide bonding→[2]

[C] gag-CO—(O—$R^1$) [3]

gag-COOH+$R^1$—OH→ester bonding→[3]

[D] gag-O—$R^{2a}$—$R^1$ [4]

$R^{2a}$, is a group derived from a spacer capable of reacting with gag-OH (e.g. HOOC—$R^3$—COOH, HOOC—$R^3$—$NH_2$) and the functional group of the photoreactive compound.

[D-1] gag-OH+HOOC—$R^3$—COOH→gag-O—CO—$R^3$—COOH

[D-1-a] gag-O—CO—$R^3$—COOH+$R^1$—OH→gag-O—CO—$R^3$—CO—O—$R^1$ =[4a]

[D-1-b] gag-O—CO—$R^3$—COOH+$R^1$—$NH_2$ →gag-O—CO—$R^3$—CO—NH—$R^1$=[4b]

[D-2] gag-OH+HOOC—$R^3$—$NH_2$ →gag-O—CO—$R^3$—$NH_2$

[D-2-a] gag-O—CO—$R^3$—$NH_2$ +$R^1$—COOH→gag-O—CO—$R^3$—NH—CO—$R^1$=[4c]

[E] gag-CO—$R^{2b}$—$R^1$ [5]

$R^{2b}$ is a group derived from a spacer capable of reacting with gag-COOH (e.g. HO—$R^3$—COOH, HO—$R^3$—OH, HO—$R^3$—$NH_2$, $H_2N$—$R^3$—$NH_2$, $H_2N$—$R^3$—COOH) and the functional group of the photoreactive compound.

[E-0]

[E-0-a] $H_2N$—$R^3$—$NH_2$ +$R^1$—COOH→$H_2N$—$R^3$—NH—CO—$R^1$ gag-COOH+$H_2N$—$R^3$—NH—CO—$R^1$[F-1]→gag-CO—NH—$R^3$—NH—CO—$R^1$=[5-1]

[E-0-b] RNH—$R^3$—$NH_2$ +$R^1$—COOH→H RNH—$R^3$—NH—CO—$R^1$[F-2]

RNH—$R^3$—NH—CO—$R^1$[F-2] →$H_2N$—$R^3$—NH—CO—$R^1$ gag-COOH+$H_2N$—$R^3$—NH—CO—$R^1$[F-1] or )

[F-2]

→gag-CO—NH—$R^3$—NH—CO—RI=[5-1]

R is a protective group.

[E-1] gag-COOH+HO—$R^3$—COOH→gag-CO—O—$R^3$—COOH

[E-1-a] gag-C—O—$R^3$—COOH+RI—OH→gag-CO—O—$R^3$—CO—O—RI=[5a]

[E-1-b] gag-CO—O—$R^3$—COOH+$R^1$—$NH_2$ →gag-CO—O—$R^3$—CO—NH—$R^1$ =[5]

[E-2] gag-COOH+HO—$R^3$—OH→gag-CO—O—$R^3$—OH

[E-2-a] gag-CO—O—$R^3$—OH+RP—COOH→gag-CO—O—$R^3$—O—CO—RI=[5c]

[E-3] gag-COOH+HO—$R^3$—$NH_2$ →gag-CO—O—$R^3$—$NH_2$

[E-3-a] gag-CO—O—R—$NH_2$ —$R^1$—COOH→gag-CO—O—$R^3$—NH—CO—$R^1$=[5d]

[E-4] gag-COOH+$H_2N$—$R^3$—OH→gag-CO—NH—$R^3$—OH

[E-4-a] gag-CO—NH—$R^3$—OH+$R^1$—COOH→gag-CO—NH—$R^3$—O—CO—$R^1$=[5e]

[E-5] gag-COOH+$H_2N$—$R^3$—$NH_2$ →gag-CO—NH—$R^3$—$NH_2$

[E-5-a] gag-CO—NH—$R^3$—$NH_2$ +$R^1$—COOH→gag-CO—NH—$R^3$—NH—CO—R=[5f]

[E-6] gag-COOH+$H_2N$—$R^3$—COOH→gag-CO—NH—$R^3$—COOH

[E-6-a] gag-CO—NH—$R^3$—COOH+$R^1$—OH→gag-CO—NH—$R^3$—CO—O—$R^1$=[5g]

[E-6-b] gag-CO—NH—$^R3$—COOH+$R^1$—$NH_2$ gag-CO—NH—$R^3$—CO—NH—$R^1$=[5h]

$R^3$ is preferably one of the following:

$R^{3a}$: —$(CH_2)_n$- (n=1 to 10);

$R^{3b}$: —$(CH_2)_p$CHY—(Y being COOH or $NH_2$ and p being 1 to 10);

$R^{3c}$: —$(CH_2)_m$—$C_6H_4$—$(CH_2)_l$—(m=1 to 10, l=1 to 10).

While, in the above examples, only one spacer is used, a plurality of spacers may also be used.

The above-mentioned photoreactive compound [F-1] or [F-2] may be used in lieu of $R^1$—$NH_2$ in preparing the product of formula [4b], [5b] or [5h].

In principle, $R^1$, which is a photoreactive group, may be any group provided that it is capable of at least dimerizing intermolecularly and/or intramolecularly upon exposure to light under formation of a cyclobutane ring.

In each of the above formulas, —COOH may take the form of a reactive derivative (e.g. halide, acid anhydride, active ester) capable of reacting with the hydroxyl or amino group.

As particularly preferred examples of $R^1$—CO—which is found in the formulas [1], [4c], [5c] to [5f], etc., there may be mentioned groups of the following formulas:

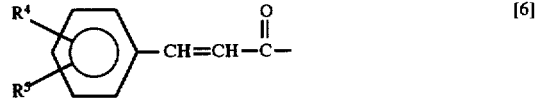

[6]

where $R^4$ and $R^5$ may be the same or different and each is a hydrogen atom, a lower alkyl, lower alkoxyl, nitro or amino group;

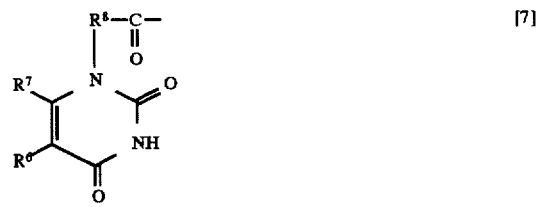

[7]

where $R^6$ is a hydrogen or halogen atom or a lower alkyl or halo-lower alkyl group, $R^7$ is a hydrogen or halogen atom or a cyano, carboxyl, lower alkoxycarbonyl, lower alkyl or halo-lower alkyl group, and $R^8$ is a lower alkylene group;

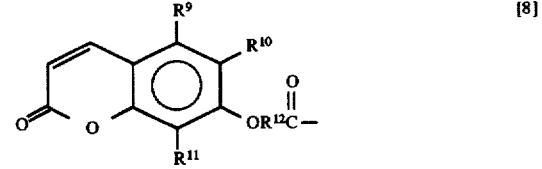

[8]

where $R^9$, $R^{10}$ and $R^{11}$ may be the same or different and each independently is a hydrogen atom or a lower alkyl group, and $R^2$ is a lower alkylene group.

Groups of the above formulas [6] to [8] are particularly preferred as $R^{1a}$—CO—($R^{1a}$ being a photoreactive group) in $R^1$a—CO—NH—$R^3$—NH according to formula [2] and as $R^1$—CO—in formula [5-1], and $R^{3a}$ or $R^{3b}$ is preferred as $R^3$. When $R^3$ is $R^{3b}$, COOH is preferred as Y.

As preferred examples of R¹—O— occurring in formulas [3], [4a], [5a], [5g], etc., there may be mentioned residues of the following formulas:

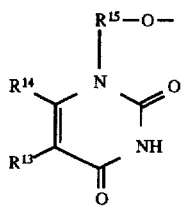 [9]

where R¹³ is a hydrogen or halogen atom or a lower alkyl or halo-lower alkyl group, R¹⁴ is a hydrogen or halogen atom or a cyano, carboxyl, lower alkoxycarbonyl, lower alkyl or halo-lower alkyl group, and R¹⁵ is a lower alkylene group;

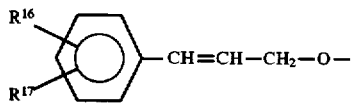 [10]

where R¹⁶ and R¹⁷ may be the same or different and each is a hydrogen atom, a lower alkyl, lower alkoxyl, nitro or amino group.

Groups of the formulas given below, for instance, may also be employed as the constituent element of R¹:

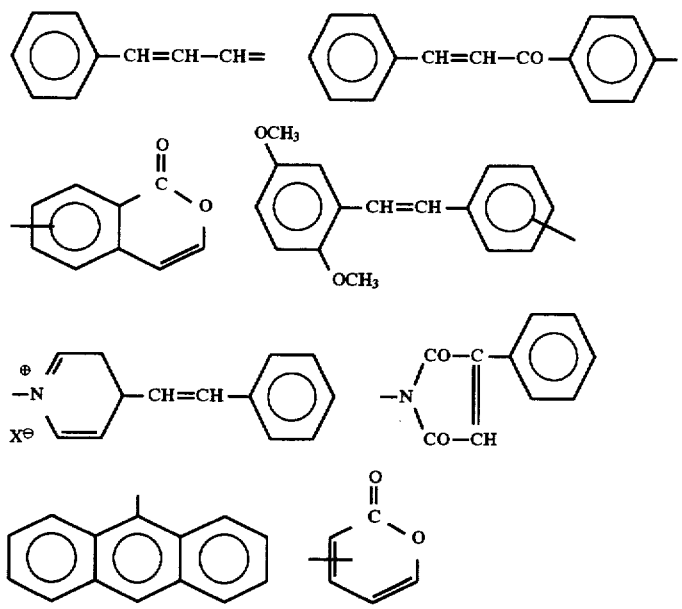

The photocurable GAG according to the invention is capable of intermolecular dimerization upon exposure to light, whereupon the photoreactive groups (i.e. groups at least containing a vinyl group) contained in the molecules of the photoreactive compound form, in pairs, cyclobutane rings according to the equation given below, giving the corresponding crosslinked GAG having a two- or three-dimensional network structure with a desired degree of crosslinking. Intramolecular dimerization may also be involved in the photocuring.

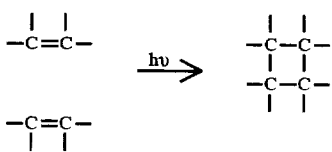

Thus, in accordance with the invention, biocompatible photocrosslinked GAGs having a desired degree of crosslinking, hence desired physical characteristics (e.g. mechanical structure supporting property, water-retaining property, hydrophilicity, lubricating property, rate of drug release) and desired biological properties (e.g. cell adhesion, biodegradability-absorbability, physiological activity) appropriate for their intended uses can be formed by selecting or controlling the photoreactive compound and GAG (e.g. chemical structure, molecular weight, etc.) and the content of the photoreactive compound (degree of substitution (DS) by the photoreactive compound), among others.

The term "degree of substitution (DS)" as used herein is defined as the number of moles of the photoreactive compound or group bound to each repeating disaccharide unit (each unit comprising a uronic acid and a hexosamine) of GAG. Thus, for instance, hyaluronic acid having four hydroxyl groups (substitutable hydroxyl groups) per such disaccharide unit, when modified by a photoreactive compound or group on all the hydroxyl groups, gives a DS of 4 whereas the three hydroxyl groups per disaccharide unit of chondroitin sulfate, upon complete modification thereof by a photoreactive compound or group, results in a DS of 3.

The term "glycosaminoglycan" or "GAG" as used herein includes colominic acid, hyaluronic acid (HA), chondroitin, chondroitin sulfate (CS), teichuronic acid, dermatan sulfate, heparin, heparan sulfate, keratosulfate (keratan sulfate), keratopolysulfate, chitin, chitosan, and derivatives thereof (acyl derivatives, polysulfates, desulfation products, deacylation products, etc.). The term "lower" means that the carbon chain in question, which may be straight or branched, is composed of 1 to 6 carbon atoms. The term "halogen atom" includes chlorine, bromine and iodine atoms and the term "halo" is used to indicate that one or more hydrogen atoms have been substituted by such halogen atoms.

In the combinations of formula [6] with formulas [1], [4c], [5-1], [5c] to [5f], etc., $R^1CO$— is, for example, the residue derived from a substituted or unsubstituted cinnamic acid or a reactive derivative thereof. As the substituted cinnamic acid residue, there may be mentioned the ones having one or two lower alkyl, lower alkoxyl, nitro or amino groups in any positions of the benzene ring. The $R^1CO$— derived from cinnamic acid is particularly preferred, however.

In the combinations of formula [7] with formulas [1], [4c], [5-1], [5c] to [5f], etc., $R^1CO$— is, for instance, the residue derived from a uracil derivative having a carboxyalkyl group as a substituent in position 1 or a reactive derivative thereof, with a hydrogen or halogen atom or a lower alkyl or halo-lower alkyl group, represented by $R^6$, in position 5 of the pyrimidine ring, a hydrogen or halogen atom or a cyano, carboxyl, lower alkoxycarbonyl, lower alkyl or halo-lower alkyl group, represented by $R^7$, in position 6 and a lower alkylene group, $R^8$, as derived from the carboxyalkyl group and forming an ester bond with a hydroxyl group of gag, in position 1. In particular, the 1-(2-carboxyethyl)thymine-derived $R^1CO$— is preferred.

In the combinations of formula [8] with formulas [1], [4c], [5-1], [5c] to [5f], etc., $R^1CO$— is, for instance, the residue derived from a 7-carboxyalkoxyl-substituted coumarin derivative or a reactive derivative thereof, with the positions 5, 6 and 8 of the coumarin ring each independently having a hydrogen atom or a lower alkcyl group, represented by $R^9$, $R^{10}$ and $R^{11}$, respectively, with a lower alkylene group, $R^{12}$, derived from the carboxyalkoxyl group and forming an ester bond with a hydroxyl group of gag, in position 7. A particularly preferred $R^1CO$— group is the 7-coumaryloxyacetic acid-derived one.

In the combinations of formula [10] with formulas [3], [4a], [5a], [5g], etc., $R^1O$— is the residue derived from a 1-hydroxyalkyl-substituted uracil derivative or a reactive derivative thereof, with a hydrogen or halogen atom or a lower alkyl or halo-lower alkyl group, represented by $R^{13}$, in position 5 of the pyrimidine ring, a hydrogen or halogen atom or a cyano, carboxyl, lower alkoxycarbonyl, lower alkyl or halo-lower alkyl group, represented by $R^{14}$, in position 6 and a lower alkylene group, $R^{15}$, derived from the hydroxyalkyl group and forming an ester bond with the carboxyl group of gag, in position 1.

In the combinations of formula [11] with formulas [3], [4a], [5a], [5g], etc., $R^1O$— is, for instance, the residue derived from a substituted or unsubstituted cinnamyl alcohol or a reactive derivative thereof. The substituted cinnamyl alcohol residue is, for example, one having one or two lower alkyl, lower alkoxyl, nitro or amino groups in any positions of the benzene ring.

[Starting compounds]

GAGs

The GAGs are not limited in origin or molecular weight. GAGs, as selected according to the intended purpose, are used either singly or in the form of a mixture of two or more of them. While GAGs of natural origin (extract of animal organs, fermentation products, etc.) are generally used, GAGs chemically or enzymatically synthesized or GAGs synthesized by semisynthetic processes may also be used when necessary. Products derived from these by functional group modification may be used as well.

The GAG may be reacted with the photoreactive compound as it is, but it is generally used in the form of a salt: with alkali metal such as sodium, potassium, etc., alkali earth metal such as magnesium, calcium, etc., tertiary amine such as tri-n-butylamine, triethylamine, pyridine, etc. and the like.

When the photoreactive compound to be bound to the GAG is water-insoluble, the photoreactive compound is added to the organic solvent containing the GAG to carry out the reaction.

The organic solvent containing the GAG is prepared by, for example, treating an aqueous solution of a sodium salt of GAG with a cation exchanger to form carboxyl radicals or sulfate radicals, adding thereto a water-miscible organic solvent [e.g. dimethylformamide (DMF), dimethylsulfoxide (DMSO), hexamethylphosphoramide (HMPA), pyridine, or the like] and tertiary amine (e.g. tri-n-butylamine) to form an amine salt of the GAG and removing the water by distillation.

When the photoreactive compound is water-soluble, the reaction can be carried out by adding the photoreactive compound to an aqueous solution of GAG (e.g. sodium salt).

Photoreactive Compounds

The photoreactive compounds, which are subjected to bond formation with such a group as —OH, —COOH or —$NH_2$ of GAGS; or of a spacer bound or capable of binding to GAGs, as mentioned above, have such a group as —OH, —COOH or —$NH_2$.

(1) When —COOH is the functional group:

The photoreactive compounds are bound to GAGs or to spacer groups under ester formation, as in formulas [1], [4c], [5-1], [5c], [5d], [5e] and [5f] and include compounds having chemical structure where OH or a halogen, for instance, is bound to groups of formula [6] to [8], namely substituted or unsubstituted cinnamic acids, 1-carboxyalkyl-substituted uracils and 7-carboxyalkoxyl-substituted coumarins (7-coumaryloxy carboxylic acids), and reactive derivatives thereof. As the reactive derivatives, there may be mentioned acid halides (e.g. acid chloride, etc.) and acid anhydrides.

The acid halides of the above-mentioned 7-coumaryloxy carboxylic acids can be synthesized by condensing the corresponding, optionally substituted, 7-hydroxycoumarin with a halo-carboxylic acid ester in the presence of an alkali and hydrolyzing the resulting 7-coumaryloxy carboxylic acid ester to obtain 7-coumaryloxy carboxylic acid, or by condensing the corresponding, optionally substituted 7-hydroxycoumarin with a halo-carboxylic acid to obtain 7-coumaryloxy carboxylic acid., and then reacting thus obtained 7-coumaryloxy carboxylic acid corresponding to formula [1], which may optionally have a substituent or substituents, with a thionyl halide (cf. e.g. JP-A-3-48674).

(2) When —$NH_2$ is the functional group:

Photoreactive compounds of the formula [G] given below can be obtained by reacting the above-mentioned substituted or unsubstituted cinnamic acid, 1-carboxyalkyl-substituted uracils or 7-carboxyalkoxyl-substituted coumarins (7-coumaryloxy carboxylic acids), or reactive derivatives thereof with a compound of the formula [X-1] or a compound [X-2] derived therefrom by protecting one of the amino groups with such an amino-protecting group as tert-butoxycarbonyl or benzyloxycarbonyl, followed by deprotection as necessary.

| | |
|---|---|
| $H_2N$—$R^3$—$NH_2$ | [X-1] |
| RNH—$R^3$—$NH_2$ | [X-2] |
| $H_2N$—$R^3$—NH—CO—$R^1$ | [F-1] |
| RNH—$R^3$—NH—CO—$R^1$ | [F-2] |

(3) When —OH is the functional group:

Reactive derivatives corresponding to formula [9] can be used as the photoreactive compounds. For instance, cyclic ether compounds between the positions 1 and 2 of the pyrimidine ring may be used. Specific examples are 1,2-O- ethanouracil, 1,2-O-ethanothymine, 1,2-O-ethano-5-chlorouracil, 1,2-O-ethano-5-trichloromethyluracil, 1,2-O-ethano-o6-cyanouracil, 1,2-O-ethano-6-chloromethyluracil and 1,2-O-ethano-6-trichloromethyluracil.

Mention may also be made of substituted or unsubstituted cinnamyl alcohols corresponding to formula [10].

(4) Preferred photoreactive compounds

While the photoreactive compound to be employed should be selected from among those mentioned above according to the intended purpose, photoreactive compounds derived from compounds least possibly producing adverse effects even when remaining in unreacted form in the crosslinked GAGs, for example cinnamic acid, thymine and coumarin, are preferred from the medical use viewpoint.

In the practice of the invention, the photocurable GAGs may comprise one or more photoreactive compounds bound to one and the same GAG molecule or to a plurality of different GAG molecules. This applies to the above formulas [1] to [3] as well. Therefore, it is to be noted that the crosslinked (GAGs of the present invention include, within the meaning thereof, products obtained by photocrosslinking of such photocurable GAGs.

Reactions (introduction of photoreactive groups)

(1) Esterification reaction with gag—OH

An appropriate tertiary amine salt (e.g. tri-n-butylamine salt, triethylamine salt, pyridine salt, etc.) of a GAG is dissolved in an appropriate solvent (e.g. DMF, pyridine, DMSO, HMPA, etc.) and hydroxyl groups of the GAG are subjected to esterification reaction with a substituted or unsubstituted cinnamic acid having the partial structure of formula [6] in an amount of 0.5 to 5 moles per mole of the hydroxyl groups of the GAG or a reactive derivative thereof, for example an acid halide, in the presence of a basic catalyst (e.g. anhydrous pyridine etc.) or with $R^1COOH$ having the partial structure of formula [7] or [8] or a reactive derivative thereof in the presence of a basic catalyst (e.g. 2-chloro-1-methylpyridinium iodide, pyridine, etc.), at 0 to 100° C., preferably 70° to 90° C., for several tens of minutes to several tens of hours, preferably 1 to 10 hours, to give a photocurable GAG of the invention.

The degree of substitution (DS) in each photocurable GAG can be controlled as desired by controlling the reaction conditions. For instance, the DS can be increased by increasing the mole ratio of $R^1COOH$ or a reactive derivative thereof relative to the starting GAG and/or prolonging the reaction time.

After the reaction, sodium acetate-saturated ethanol, ethanol, or methanol, for instance, is added to the reaction mixture, and the resulting precipitate is collected by filtration, washed with ethanol or methanol and then dried under reduced pressure, whereby the desired product can be obtained in the form of a white powder.

The reaction for production of the compound of formula [5c] or [5e] can be performed in essentially the same manner as mentioned above.

Some specific examples of the thus-obtainable photocurable GAG where each disaccharide unit is substituted with one molecule of a photoreactive compound are shown below by structural formulas of the unit. Structurally different building units, for example units differing in the number of photoreactive groups bound thereto and/or positions of their binding, may occur in one and the same molecule. 1) Photocurable GAG (HA—Cin) resulting from introduction of cinnamic acid into hyaluronic acid

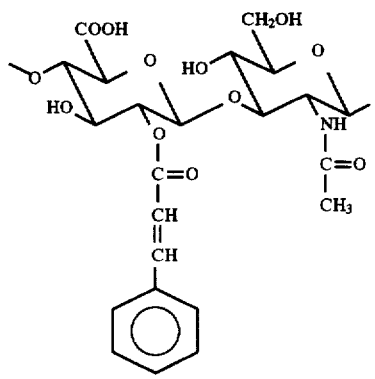

2) Photocurable GAG (HA-Thym) resulting from introduction of 1-(2-carboxyethyl)thymine into hyaluronic acid

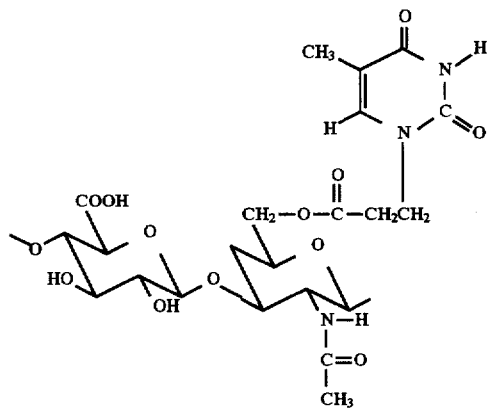

3) Photocurable GAG resulting from introduction of 7-coumaryloxyacetic acid into chondroitin sulfate

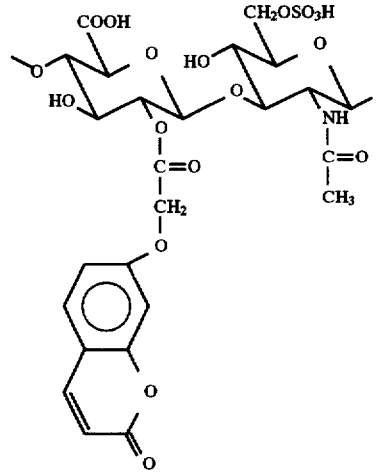

(2) Amidation with gag-COOH [in particular when a photoreactive compound is bound to a spacer group]; cf. formula [5-1]

(2-1): When $R^3 = R^{3a}$

When the compound of formula [X-1] or [X-2] is an alkylenediamine (e.g. ethylenediamine), an appropriate tertiary amine salt (e.g. tri-n-butylamine salt, triethylamine salt, pyridine salt, etc.) of a GAG is dissolved in an appropriate solvent (e.g. DMF, pyridine, DMSO, HMPA, etc.), as in the above process (1), then an amount, slightly excessive in the number of moles relative to that of the carboxyl group of the GAG, of a hydroxy compound (e.g. N-hydroxysuccinimide, N-hydroxyphthalimide, etc.) and a condensing agent (e.g. dicyclohexylcarbodiimide, 1-ethyl-3-(dimethylaminopropyl)carbodiimide, etc.) are added, and the reaction is carried out at 0° to 50° C. for 1 to 20 hours to give a modified GAG activated at its carboxyl groups. Then, the thus modified GAG and the amino group of the compound of formula [F-1] or [F-2] are subjected to amidation reaction at 0° to 50° C. for 30 minutes to 20 hours to give a photocurable GAG.

Photocurable GAGs can also be prepared by using an aqueous solution of a GAG and subjecting the amino group of a compound of formula [F-1] or [F-2] and the carboxyl groups of the GAG to amidation reaction at 0° to 50° C. for 1 to 20 hours in the presence of a condensing agent [e.g. a water-soluble carbodiimide such as 1-ethyl-3-(dimethylaminopropyl)-carbodiimide].

(2-2): When $R^3 = R^{3b}$ (Y=COOH):

When the compound of formula [X-11 or [X-2] is, for instance, a basic amino acid (e.g. L-lysine), a GAG is used in the form of an aqueous solution and the amino group of a compound of formula [F-1] or [F-2] and the carboxyl groups of the GAG are subjected to amidation reaction at 0° to 50° C. in the presence of a condensing agent [e.g. a water-soluble carbodiimide such as 1-ethyl-3-(dimethylaminopropyl)-carbodiimide] to give a photocurable GAG.

Photocurable GAGs can also be prepared by reacting a GAG in the form of an appropriate tertiary amine salt with a hydroxy compound such as N-hydroxysuccinimide in an appropriate solvent such as DMF in the presence of a condensing agent such as dicylohexylcarbodiimide, as in process (2-1), and subjecting the resulting GAG activated at its carboxyl groups to amidation reaction with the amino group of a compound of formula [F-1] or [F-2].

The reaction involved in formula [2], [4b], [5b] or [5h] can be performed in essentially the same manner as mentioned above.

(3) Esterification with gag-COOH

Like in the above-mentioned process (1), an appropriate tertiary amine salt (e.g. tri-n-butylamine salt, triethylamine salt, pyridine salt, etc.) of a GAG is dissolved in an appropriate solvent (e.g. DMF, pyridine, DMSO, HMPA, etc.), and a reactive derivative of a uracil derivative of formula (9], for example a cyclic ether compound, or a substituted or unsubstituted cinnamyl alcohol of formula [10] or a reactive derivative thereof and the carboxyl groups of the GAG are subjected to esterification reaction at 0° to 100° C. in the presence of a basic catalyst (e.g. anhydrous pyridine etc.).

The reaction involved in formula [4a], [5a] or [5g] can be carried out in essentially the same manner as mentioned above.

Isolation and Purification of Photocurable GAGs

After the above reactions, the photocurable GAGs formed can be isolated and purified by any of the methods generally employed for the isolation and purification of GAGs, without any particular limitation.

Thus, for instance, photocurable GAGs, namely the desired products, can be separated from unreacted GAGs or unreacted photoreactive compounds and can be purified by such methods as chromatography using an anion or cation exchanger, the method utilizing the difference in solubility in an organic solvent (e.g. alcohol precipitation method), salting out or dialysis.

While those crosslinked glycosaminoglycans that are known in the art occur as gels or solids and therefore unreacted materials, catalysts, contaminant microorganisms, pyrogens and other impurities can hardly be eliminated therefrom, the photocurable GAGs of the present invention are soluble in water and/or an organic solvent and therefore can be readily purified. Since the thus-purified photocurable GAGs, upon exposure to light, can undergo intermolecular or intramolecular dimerization of the photoreactive groups, crosslinked GAGs minimally contaminated with unreacted materials, catalysts, contaminant microorganisms, pyrogens, etc. can be readily produced.

Physical Characteristics of Photocurable GAGs

The physical characteristics of the photocurable GAGs synthesized and purified in the above manner may vary depending on the GAG used as the starting material, the molecular weight thereof, the photoreactive compound employed, the amount thereof and other factors and can be adjusted as desired so that they can be suited for the intended purposes. Generally, they have a molecular weight within the range of 4,000 to 2,000,000, preferably 10,000 to 1,000,000, and a degree of substitution (DS) by photoreactive groups within the range of 0.1 to 4.0, preferably 0.1 to 3.0, and are soluble in water and/or organic solvents. The solubility can be controlled as desired. Generally, an increase in DS results in a decreased solubility in water but in an increased solubility in organic solvents such as DMF. When the photoreactive group is a cinnamic acid derivative of formula [6], a 7-coumaryloxy carboxylic acid of formula [8] or a cinnamyl alcohol derivative of formula [11], the photocurable GAGs obtained are relatively hydrophobic. On the contrary, when the photoreactive group is a uracil derivative (in particular thymine derivative) of formula [7] or [10], the photocurable GAGs produced are relatively hydrophilic.

The range of preferred DSs may vary depending on the intended use of the photocurable GAG or crosslinked GAG, and the GAG and photoreactive compound used. For producing crosslinked GAGs nonadherent to cells and using them as tissue nonadhesive materials, for instance, the DS should preferably be about 0.1 to 0.5 in the case of hyaluronic acid-cinnamic acid ester (HA-Cin), about 0.1 to 3.0 in the case of chondroitin sulfate-cinnamic acid ester (CS-Cin), about 0.2 to 1.0 in the case of hyaluronic acid-thymine derivative ester (HA-Thym), and about 0.2 to 1.0 in the case of chondroitin sulfate-thymine derivative ester (CS-Thym), for instance. For embedding a biological substance, a drug or the like in the three-dimensional network structure of crosslinked GAGs to thereby attain controlled release thereof, a DS of 1.0 to 2.5 is preferred for each of the crosslinked GAGs mentioned above.

More specifically, when the photocurable GAG is a photocurable hyaluronic acid derivative of the formula [1], the molecular weight is preferably within the range of 100,000 to 1,000,000 and the degree of substitution by photoreactive compound (DS) is preferably within the range or 0.1 to 3.0. When the photocurable GAG is a photocurable chondroitin sulfate derivative of the Formula [1], the molecular weight is preferably within the range of 10,000 to 60,000, and the DS within the range of 0.1 to 3.0.

In using as medical materials, the photocurable GAGs and crosslinked GAGs may have any form. Thus, they can be used in various forms, for example solutions, gels, solids, etc. The medical materials of the invention, which are based on said photocurable GAGs or crosslinked GAGs, may contain, as desired, various solvents (e.g. water, buffer, PBS, DMF, DMSO, etc.), carriers (e.g. gauze, knit or woven fabrics, nonwoven fabrics, waddings or cotton-like materials, filaments or yarns, films, porous sponge, rubbers, plastics, metals, artificial organs, living body tissue surfaces, incisions or wounds of living body), biological substances (collagen, gelatin, heparin, chondroitin sulfate, hyaluronic acid, dermatan sulfate, etc.), drug substances, and so forth.

Molding of Photocurable GAGS (casting using a solvent) etc.

For use as medical materials, the photocurable GAGs can be molded into specific forms (film-like, tubular, granular)

or applied to, coated on, attached to or embedded in other substances or materials as described above for carriers. In such cases, the photocurable GAGs may be molded, prior to photoreaction, by dissolving them in water (preferably purified water), a buffer solution (e.g. phosphate buffer, carbonate buffer) or an organic solvent (e.g. DMF, DMSO) of medically acceptable grade, placing or spreading the solution on a flat plate or surface or in a container or the like made of glass, quartz, polyvinyl chloride, polystyrene, polyurethane or the like and drying the same by airing or some other method to give a thickness of 1 μm to 1 mm.

Production of Crosslinked GAGs (photoreaction)

Photocrosslinked GAGs can be produced by exposing the photocurable GAGs, molded in the above manner or in the form of solutions, to rays or radiations for photocrosslinking to thereby induce the photodimerization reaction. The wavelength or wavelength range to be employed may vary depending on the nature of the photoreactive group but, generally, lies within the range of about 260 to 400 nm. More specifically, rays from a high-pressure mercury lamp (450 W), for instance, can be used for the exposure (irradiation), with rays shorter in wavelength than 260–270 nm being cut off. While the exposure (reaction) period required depends on such factors as wavelength range, temperature and distance from light source, conditions under which the reaction can be driven to completion within 30 minutes are preferred. The degree of gelation (curing) can be controlled by adjusting the photocurable GAG concentration at the time of photoreaction. Generally, said concentration is 1 to 30%, preferably about 2 to 20%.

Specific examples of the dimer structure resulting from the photoreaction of photocurable GAGs are as follows.

1) When the photoreactive compound is cinnamic acid:

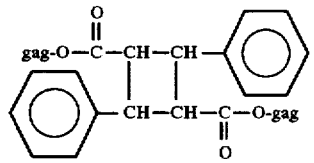

2) When the photoreactive compound is 1-(2-carboxyethyl) thymine:

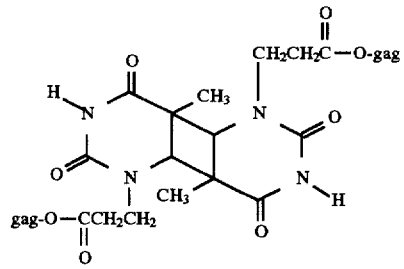

3) When the photoreactive compound is 7-coumaryloxyacetic acid:

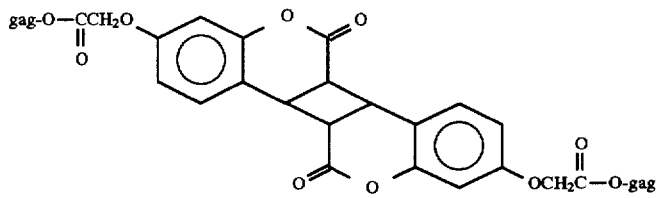

Physical Characteristics of Crosslinked GAGs

The physical characteristics of the thus-prepared crosslinked GAGs of this invention may be controlled by factors as nature of GAG, nature of photoreactive group (compound), concentration of photocurable GAG, degree of substitution (DS) by photoreactive compound, degree of crosslinking and time of photoreaction. Generally, however, they show a swelling capacity=[(weight in swollen state-weight in dry state)/weight in dry state] within a certain range (0.1 to 200) and therefore can include and retain water therein in an amount within a certain range.

The swelling capacity value decreases as the DS by the photoreactive group (compound) and the degree of crosslinking increase.

They also show an angle of contact with water within a certain range (10° to 100°). The contact angle reflects the hydrophobicity/hydrophilicity of the surface of the crosslinked GAG. An increased rate of crosslinking (dimerizing) of the photoreactive group results in an increased contact angle value, i.e. an increased level of hydrophobicity.

The degree of crosslinking, which is the percentage with which the above-mentioned photoreactive group undergoes dimerization, can be increased by increasing the DS. It can be further controlled by controlling said photoreaction.

Therefore, the biological functions of crosslinked GAGs can be controlled by varying the degree of crosslinking. For instance, such cells as endothelial cells tend to adhere to crosslinked GAGs showing a high degree of crosslinking, although this tendency may differ according to the nature of the GAG and of the photoreactive compound. Such tendency is remarkable with hyaluronic acid, which contains no sulfate group (cf. the photos referred to in the examples section), while the tendency is slight with sulfate-containing GAGs (e.g. chondroitin sulfate). In view of this, it is also possible to promote or suppress cell adhesion by using two or more GAGs combinedly. Further, this character can be utilized for differentiating, in function, the intima (innermost coat) and adventitia of an artificial blood vessel by coating the intima and adventitia with different crosslinked GAGs differing in cell adhesion tendency as prepared by selecting the GAGs and photoreactive groups and controlling the DS and/or degree of crosslinking. Thus, for instance, the intima may be rendered nonadherent to cells to thereby prevent thrombosis, while the adventitia can be made adherent to cells to thereby allow fibroblasts to adhere to it and render it impermeable to blood.

Applications as Medical Materials

The photocurable GAGs and crosslinked GAGs of the present invention can be as medical materials, inclusive of not only the materials for constituting the intima and adventitia of artificial blood vessels, as described hereinabove, but also materials for constituting artificial skills, tissue nonadhesive films or materials, wound healing promoting materials, hybrid artificial organs, artificial extracellular matrices and artificial basement membranes, among others. Furthermore, drug embedding is possible by admixing a solution of a photocurable GAG with a physiologically active substance (e.g. heparin, dermatan sulfate, heparan sulfate, anticancer agent, antiinflammatory agent, cytokine, hormone, growth factor, or enzymes such as tissue plasminogen activator, superoxide dismutase or urokinase) and subjecting the solution as such or a molding obtained therefrom to photoreaction for crosslinking. Thus, the photocurable GAGs and crosslinked GAGs can also be used as carriers for attaining controlled release of the drugs embedded therein.

Some typical applications are more specifically mentioned below.

Nonadhesive Materials

The crosslinked GAGs of this invention can be used as nonadhesive materials for preventing the undesired adhesion of surgical wounds and promoting the recovery. For instance, a crosslinked GAG film can be used by covering the abdominal wall and an intraperitoneal organ or organs (e.g. liver etc.) with the film to thereby protect the lesion (defect) in the peritoneum and thus prevent adhesion and promote wound healing. Said film can be degraded and absorbed according to the rate of wound healing.

Photocurable GAGs in the form of solutions can be used for the same purposes as mentioned above by injecting the solutions into wound sites, coating the surface with the sites and then irradiating the same with light to thereby cause formation of crosslinked films or membranes in vivo. In particular, this technique can be used to prevent adhesion and/or fill defects in endoscopic operation.

For their use as nonadhesive materials, the crosslinked GAGs (inclusive of in vivo crosslinked GAGs) should desirably have an appropriate level of strength to avoid film cracking and be resistant to tissue (cell) adhesion and biodegradable in proportion to the rate of wound healing; the biodegradation products should be substantially nontoxic even when they are absorbed by living organisms. These functions can be controlled by selecting the photocurable GAG (selection of GAG species and photoreactive compound, and of DS) and the irradiation conditions (e.g. distance from light source, kind of light source, intensity, film thickness, etc.).

Controlled Drug Release

The crosslinked GAGs of the invention can be used as materials (carriers or vehicles) for embedding drugs in their three-dimensional network structure to attain controlled release of the drugs. Thus, the drugs embedded or included can be released over a period conforming to the nature of the drugs and to the mode of application while maintaining the drug concentration within a certain range required in the environment where the drugs are released.

The rate of controlled drug release can be controlled by selecting the photocurable GAG (selection of GAG species and photoreactive group, and of DS) and the irradiation conditions (e.g. exposure time, distance from light source, wattage of light source, etc.). In this case, although the rate of release generally decreases with the increase in the molecular weight of the drug and in the electrostatic attractive force between the drug and the crosslinked GAG, said rate can be controlled to a desired level by selecting the above-mentioned photocurable GAG in combination with the drug in view of their respective chemical structures (from the viewpoints of molecular weight, electrically charged state (degree of hydrophilicity or hydrophobicity), etc.).

In this aspect of the invention, drugs are immobilized under mild conditions, so that they are stabilized in a state in which drug decomposition and activity loss, among others, are prevented as compared with the prior art.

The controlled drug release materials or preparations each comprising a crosslinked GAG and a drug embedded therein can be processed into any desired form according to the nature of the drug and the mode of application. Thus, for instance, they can be processed into films (films, coatings), jellies, gels, creams, suspensions, microcapsules, tablets, granules, powders and so forth. It is also possible to make the photocurable GAG ready for application by immersing a support (e.g. gauze, dressing material, knit or woven fabric, paper, cotton, nonwoven fabric, film, porous sponge) with a composition containing the photocurable GAG and a drug or applying said composition to such support, followed by irradiation for conversion to a crosslinked GAG. Furthermore, a composition containing the photocurable GAG and a drug can be applied to the surface or inside of such a structure as an artificial organ (e.g. artificial blood vessel, artificial heart) and then subjected to curing (crosslinking).

For embedding a drug in a crosslinked GAG of this invention, the drug is dissolved or suspended in an aqueous solution or organic solvent (e.g. DMF) solution containing about 1 to 30% by weight, for instance, of the corresponding photocurable GAG to a drug concentration of about 0.001 to 80% and, after addition of various additives as necessary, the resulting composition is molded, dried and then irradiated with light. After crosslinking, the moldings may be used as such or ground as necessary to give controlled drug release materials in the form of solids, semisolids or suspensions.

The controlled drug release materials of the invention may be used as pharmaceutical preparations. In that case, the drug-containing crosslinked GAGs can be processed, either as such or together with conventional, pharmaceutically acceptable additives such as preservatives, stabilizing agents, local anesthetics, dispersing agents, moldability modifiers, solubilizing agents and so forth, into desired dosage forms. For instance, after adjusting their average particle size to about 0.5 to 40 Mm, the drug-containing crosslinked GAGs can be used for formulating aqueous suspensions together with dispersing agents (e.g. Tween 80, HCO60 (Nippon Chemicals), carboxymethylcellulose, sodium alginate, etc.), preservatives (e.g. methylparaben, propylparaben, benzyl alcohol, chlorobutanol, etc.), isotonizing agents (e.g. sodium chloride, glycerol, sorbitol, glucose, etc.) and other additives as necessary, or preparing oleaginous suspensions by dispersing them in a vegetable oil such as olive oil, sesame oil, peanut oil, cottonseed oil or corn oil, or in propylene glycol or the like. The drug-containing crosslinked GAGs can also be used, either as such or in admixture with excipients (e.g. starch, calcium carbonate, etc.), binding agents (e.g. starch, gum arabic, carboxymethylcellulose, polyvinylpyrrolidone, hydroxypropylcellulose, etc.), lubricants (e.g. talc, magnesium stearate, polyethylene glycol 6000, etc.) and/or the like, for preparing tablets by compression molding or preparing powders, granules, etc. When filled into capsules, the powders, granules or the like give drug-containing capsules. Furthermore, the drug-containing crosslinked GAGs can be molded, as such, into films, or immobilized on some other support, to thereby give preparations for percutaneous absorption, ophthalmic preparations (e.g. corneal wound healing promoter), preparations for embedding into living bodies, or preparations to be inserted into body cavities (e.g. suppositories). These may be used as wound dressings, drug-releasing patches (e.g. adhesive tapes) and contraceptives, among others.

The drugs to be used in formulating such pharmaceutical preparations comprising the drug-containing crosslinked GAGs are not limited to any specific species but may be drugs otherwise required to be administered frequently to attain an effective blood concentration or an effective local concentration provided that they can be sufficiently retained in the network structure of the crosslinked GAGs and released in a controlled manner. The following may be mentioned as specific examples.

1. Antipyretic analgesic antiinflammatory agents such as indomethacin, mefenamic acid, acemetacin, alclofenac, ibuprofen, tiaramide hydrochloride, fenbufen, mepirizol, salicylic acid, etc.;

2. Anti-malignant tumor agents such as methotrexate, fluorouracil, vincristine sulfate, mitomycin C, actinomycin C, daunorubicin hydrochloride, etc.;

3. Antiulcer agents such as aceglutamide aluminum, L-glutamine, p-(trans-4-aminomethylcyclohexane-carbonyl)phenylpropionic acid hydrochloride, cetraxate hydrochloride, sulpiride, gefarnate, cimetidine, etc.;

4. Enzyme preparations such as chymotrypsin, streptokinase, lysozyme chloride, bromelain, urokinase, tissue plasminogen activator, etc.;

5. Antihypertensive agents such as clonidine hydrochloride, bunitrolol hydrochloride, prazosin hydrochloride, captopril, bethanidine sulfate, metoprolol tartrate, methyldopa, etc.;

6. Agents for urinary organs such as flavoxate hydrochloride etc.;

7. Anticoagulants such as heparin, heparan sulfate, thrombomodulin, dicumarol, warfarin, etc.;

8. Antiarteriosclerotic agents such as clofibrate, simfibrate, elastase, nicomol, etc.;

9. Agents for circulatory organs such as nicardipine hydrochloride, nimodipine hydrochloride, cytochrome C, tocopherol nicotinate, etc.;

10. Steroids such as hydrocortisone, prednisolone, dexamethasone, betamethasone, etc.;

11. Wound healing promoters such as growth factors, collagen, etc. (cf. JP-A-60-222425).

In addition, mention may also be made of physiologically active polypeptides, hormones, tuberculostats, hemostyptics, antidiabetic agents, vasodilating agents, antiarrhythmic agents, cardiacs, antiallergic agents, antidepressants, antiepileptics, muscle relaxants, antitussive expectorants, antibiotics, and the like.

The controlled drug release materials of this invention can be used as medical materials for making constituents (e.g. surfaces) of such structures as artificial organs (e.g. artificial blood vessel, artificial heart, etc.). In this case, they are particularly useful as medial materials constituting surfaces which are to come into contact with blood, where an anticoagulant (e.g. heparin, heparan sulfate, thrombomodulin), a fibrinolysis activator (e.g. tissue plasminogen activator, urokinase) and/or an antiplatelet substance may be embedded in the crosslinked GAGs for attaining controlled release of these substances and rendering said surfaces antithrombotic.

Artificial Extracellular Matrices and Artificial Basement Membranes

The photocurable GAGs of the invention, either in admixture with cell adhesive proteins such as collagen, gelatin and fibronectin or after chemically binding such proteins thereto, may be converted to crosslinked GAGs which can be utilized as artificial extracellular matrices or artificial basement membranes for allowing adhesion and growth of cells (endothelial cells, epithelial cells, smooth muscle cells, etc.) (cf. JP-A-1-124465, 61-128974 and 62-270162). These can be used as hybrid type artificial organs (artificial blood vessel, artificial skin, etc.)

The following examples are further illustrative of the present invention but are by no means limitative of the scope thereof.

In the examples, some typical physical characteristics and a biological function were measured or evaluated by the methods mentioned below using the apparatus specified below. $^1$H NMR spectra were measured using a JOEL JNM-JX270 FTNMR spectrometer, and UV/VIS spectra using a JASCO Ubest-30UV/VIS spectrometer.

The degree of substitution (DS) for each photo-. reactive compound was calculated based on the $^1$H NMR or UV data. It was also determined by comparison with the UV absorption data for low-molecular-weight model compounds (GAG degradation products) with the photoreactive compound bound thereto.

The swelling capacity of each crosslinked GAG derivative was determined as follows:

Swelling capacity=[Wg(swollen)−Wg(dry)]/Wg(dry) where Wg(dry) is the weight of a dried crosslinked GAG film prepared by photoirradiation and Wg(swollen) is the weight of the film after 24 hours of immersion in purified water.

As for the contact angle, advancing contact angles and receding contact angles were measured by the liquid drop method using a contact angle goniometer (static Kyowa contact angle meter CA-D, Kyowa Kaimen Kagaku K. K.). When the term "advancing contact angle".

Endothelial cell adhesion experiments were performed as follows. Each photocurable GAG was made into a film by casting from a solvent, and the film was immobilized on the bottom of a tissue culture dish made of polystyrene (TCPS). This was seeded with bovine aorta-derived endothelial cells under sterile conditions. The culture medium used was Dulbecco's modified Eagle medium (DMEM) supplemented with 10–15% fetal calf serum (FCS). Whether cell adhesion had occurred or not was judged by observation under a phase contrast microscope after 24 hours of incubation at 37° C. For cell growth judgment, the growth rate after 1–2 days was used.

EXAMPLE 1

Preparation of hyaluronic acid-cinnamic acid ester and preparation of crosslinked hyaluronic acid by photoreaction thereof (1) Preparation of Hyaluronic Acid-cinnamic Acid Ester Anhydrous pyridine (30 ml) was added to a solution of hyaluronic acid (molecular weight 880,000) tri-n-butylamine salt in dimethylformamide (DMF) (150 mg/35 ml), followed by addition of 26.64 mg of cinnamoyl chloride with vigorous stirring at room temperature. Esterification was allowed to proceed at 750° C. for 2 hours, then ethanol saturated with sodium acetate was added to the reaction mixture, and the resulting precipitate was collected and thoroughly washed with ethanol for removing unreacted cinnamoyl chloride, to give cinnamic acid ester of hyaluronic acid.

| Lot: | HA—Cin-3 |
| --- | --- |
| Yield: | 95.6 mg |
| Bound cinnamic acid: | 11.0 wt. % (based on $^1$H NMR spectrum) |
| DS: | 0.50 |

A $^1$H NMR spectrum of the above product is shown in FIG. 1. Typical characteristic absorptions are as follows:

6–8 ppm: Ascribable to protons of cinnamic acid benzene ring and of cinnamic acid double bond;

2 ppm: Ascribable to methyl protons of hyaluronic acid N-acetyl groups.

The ratio between the numbers of these protons was calculated and used to determine the bound cinnamic acid amount and DS given above.

(2) Preparation of a Cured (crosslinked) Hyaluronic Acid Film

A solution of 30 mg of the lot HA-Cin-3 in DMF was placed on a slide glass (24 mm×24 mm) and dried using sterile air warmed to 40° C. The film formed was exposed to irradiation of a 450-W high pressure mercury lamp through a pyrex-covered water filter, which was used to cut off the wavelength below 270 nm. Thus was obtained a cured (i.e. crosslinked) hyaluronic acid film.

Figure 2:
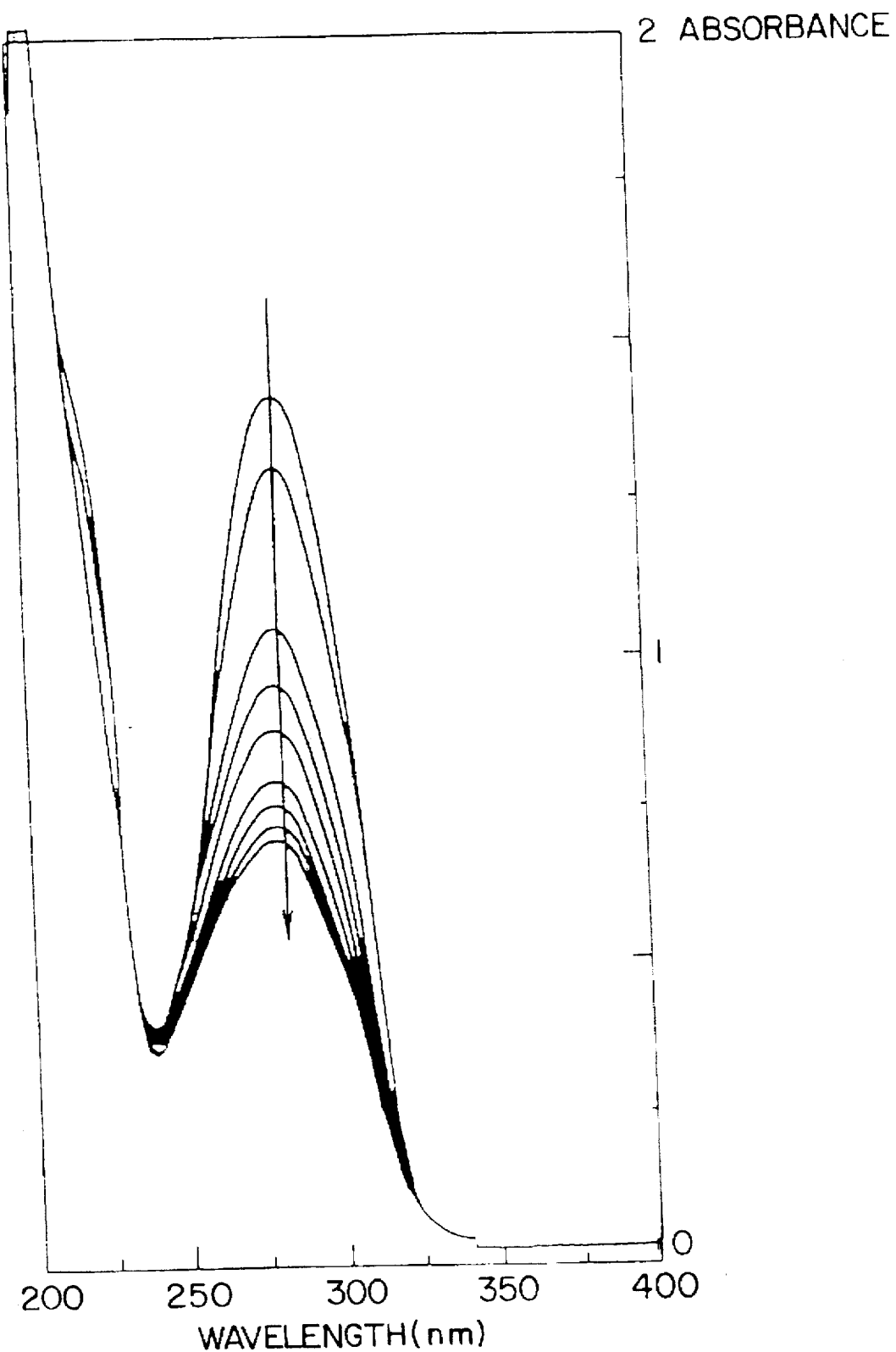
FIG. 2 shows UV/VIS spectra illustrating the attenuating absorbance at 279 nm as resulting from exposure to light in the crosslinked hyaluronic acid film preparation in Example 1.

The absorption peak at 279 nm attenuated upon irradiation (FIG. 2). The irradiation was discontinued when the percent attenuation became constant (irradiation period: 30 minutes).

Lot: HA-Cin-3-2

EXAMPLE 2

Hyaluronic acid-cinnamic acid esters were prepared using the same materials and procedure as employed in Example 1 except that the quantity ratio between hyaluronic acid and cinnamic acid was varied as indicated below in Table 1 (the quantity of hyaluronic acid was always 150 mg). Further, cured (crosslinked) hyaluronic acid films were prepared by the procedure of Example 1.

TABLE 1

| | Hyaluronic acid-cinnamic acid ester | | | Crosslinked hyaluronic acid |
| --- | --- | --- | --- | --- |
| Lot | Yield | Bound cinnamic acid | DS | Lot |
| HA—Cin- 1 | 92.3 mg | 2.0 wt % | 0.10 | HA—Cin- 1-2 |
| 2 | 97.3 | 6.5 | 0.35 | 2-2 |
| 4 | 111.4 | 14.0 | 0.87 | 4-2 |
| 5 | 117.0 | 22.5 | 1.28 | 5-2 |
| 6 | 139.2 | 36.0 | 2.43 | 6-2 |
| 7 | 149.7 | 46.0 | 3.65 | 7-2 |

EXAMPLE 3

Contact Angles of Cured (crosslinked) Hyaluronic Acid Films

Figure 3:
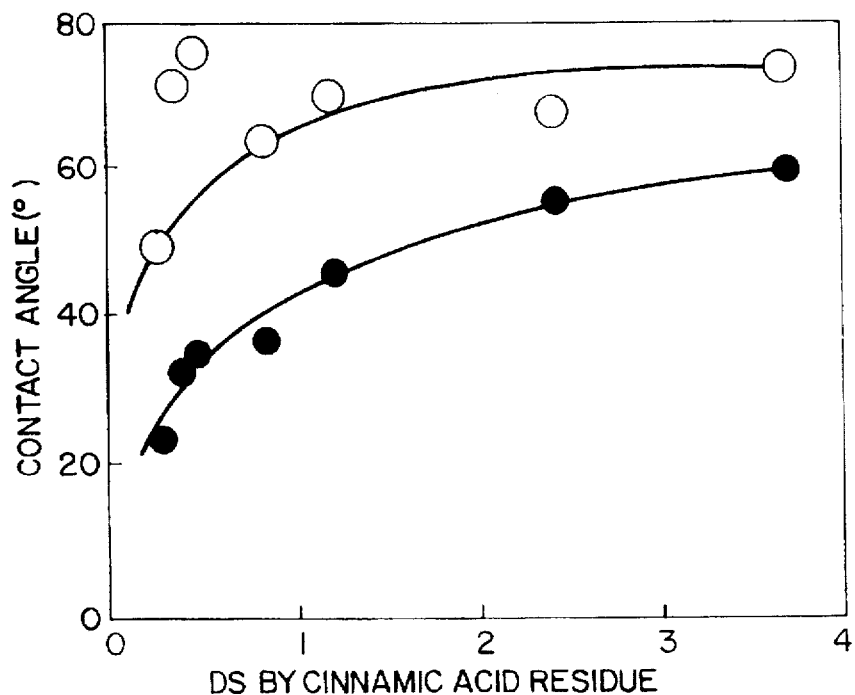
FIG. 3 graphically shows the dependency of the contact angle on the degree of substitution (DS) by the cinnamic acid residue among various crosslinked hyaluronic acid films.

Each of the cured hyaluronic acid films obtained in Examples 1 and 2 was measured for forwarding and receding contact angles. The results are shown in FIG. 3. Both contact angles clearly increased as the DS by the cinnamic acid residue increased.

An increase in contact angle reflects an increase in film surface hydrophobicity.

EXAMPLE 4

Swelling capacity evaluation of cured (crosslinked) hyaluronic acid films

Each of the cured hyaluronic acid films obtained in Examples 1 and 2 was measured for swelling capacity by allowing it to swell in purified water for 20 hours. The results are shown in FIG. 4.

Figure 4:
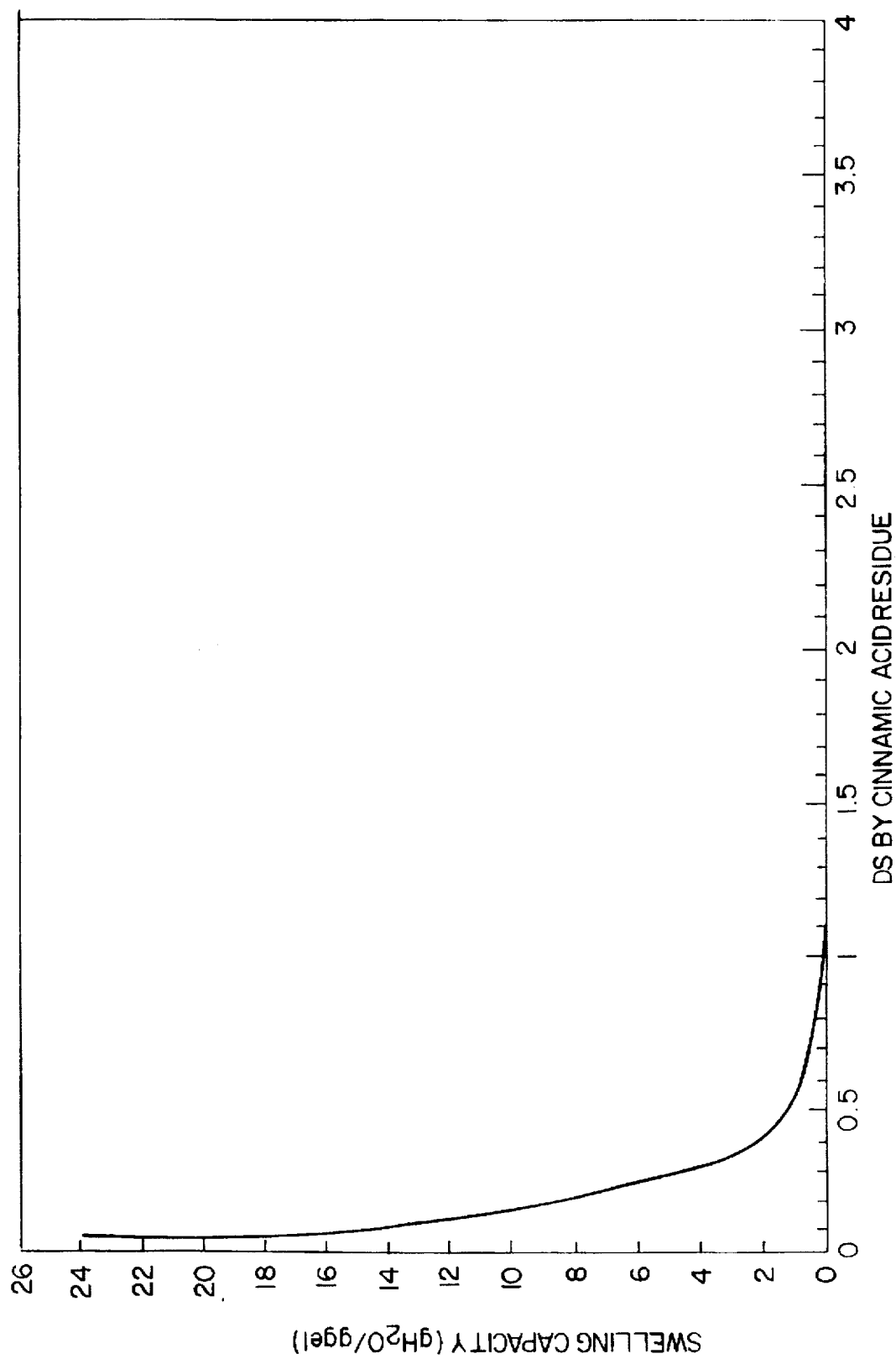
FIG. 4 graphically shows the dependency of the swelling capacity on the DS by the cinnamic acid residue among various crosslinked hyaluronic acid films.
Figure 5A:
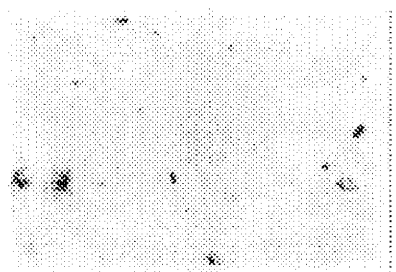
FIGS. 5a, 5b, 5c and 5d are photographs showing cell morphologieas, which illustrate differences in endothelial cell adhesion as resulting from differences in the DS by the cinnamic acid residue among crosslinked hyaluronic acid films.
Figure 5B:
Figure 5C:
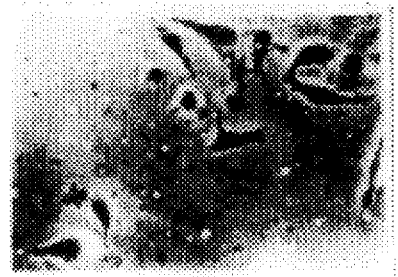
Figure 5D:

As shown in FIG. 4, the swelling capacity decreased as the DS by the cinnamic acid residue increased.

A decrease in swelling capacity reflects an increase in hydrophobicity of the film as a whole.

EXAMPLE 5

Adhesion of endothelial cells to cured (crosslinked) hyaluronic acid films

The adhesion or attachment of endothelial cells to the cured hyaluronic acid films obtained in Example 1 and 2 [lots: HA-Cin-3-2 (DS=0.5), 4-2 (DS=0.87), 5-2 (DS=1.28), and 6-2 (DS=2.43)] were evaluated after 24 hours of incubation. The results are shown in FIGS. 5a to 5d (photos).

As shown in FIGS. 5a to 5d, the adhesion of endothelial cells tended to increase with the increase in the DS by the cinnamic acid residue.

The film HA-Cin-3-2 with DS=0.5 showed a sufficient cell nonadhesive effect and was thus found to have fundamental characteristics required of a tissue nonadhesive material.

The data obtained are also useful as fundamental data to be referred to in preparing artificial extracellular matrices or artificial basement membranes using the cross:linked GAGs of the invention in combination with cell adhesive proteins such as collagen, gelatin and fibronectin and allowing endothelial cells, epithelial cells, smooth muscle cells or the like cells to adhere to and grow on said matrices or membranes to provide hybrid type artificial organs (artificial blood vessel, artificial skin, etc.).

EXAMPLE 6

Preparation of Chondroitin Sulfate-cinnamic Acid Ester and Preparation of Crosslinked Chondroitin Sulfate by Photoreaction thereof (1) Preparation of Chondroitin Sulfate-cinnamic Acid Ester Anhydrous pyridine (30 ml) was added to a solution of tri-n-butylamine salt of chondroitin sulfate (mol. wt.=60,000) in D{F. (247 mg/15 ml). To the mixture was added, with vigorous stirring at room temperature, 19.78 mg of cinnamoyl chloride. The reaction was carried out at 75° C. for 2 hours. Ethanol saturated with sodium acetate was added to the reaction mixture and the resulting precipitate was collected, thoroughly washed with ethanol and dried under reduced pressure.

| Lot: | CS—Cin-1 |
| --- | --- |
| Yield: | 152 mg |
| Bound cinnamic acid: | 7.52 wt. % |
| DS: | 0.33 |

(2) Preparation of Crosslinked Chondroitin Sulfate Film

The product CS-Cin-1 prepared in the above step (1) was dissolved in phosphate buffer to a concentration of 15% and then caused to gel by irradiation using the same mercury lamp as used in Example 1.

Lot: CS-Cin-1-2

EXAMPLE 7

Chondroitin sulfate-cinnamic acid esters were prepared using the same materials and procedure as used in Example 6 except that the quantity ratio between chondroitin sulfate and cinnamic acid was varied as indicated in Table 2 (the quantity of chondroitin sulfate was always 247 mg) and crosslinked chondroitin sulfate films were prepared therefrom by the same procedure as used in Example 1.

TABLE 2

| Lot | Chondroitin sulfate-cinnamic acid ester | | Crosslinked chondroitin sulfate | |
| --- | --- | --- | --- | --- |
| | Yield | Bound cinnamic acid | DS | Lot |
| CS—Cin- 2 | 165.7 mg | 11.59 wt % | 0.51 | CS—Cin- 2-2 |
| 3 | 170.0 | 14.0 | 0.65 | 3-2 |
| 4 | 195.3 | 25.8 | 1.37 | 4-2 |
| 5 | 233.8 | 38.6 | 2.43 | 5-2 |

Figure 6:
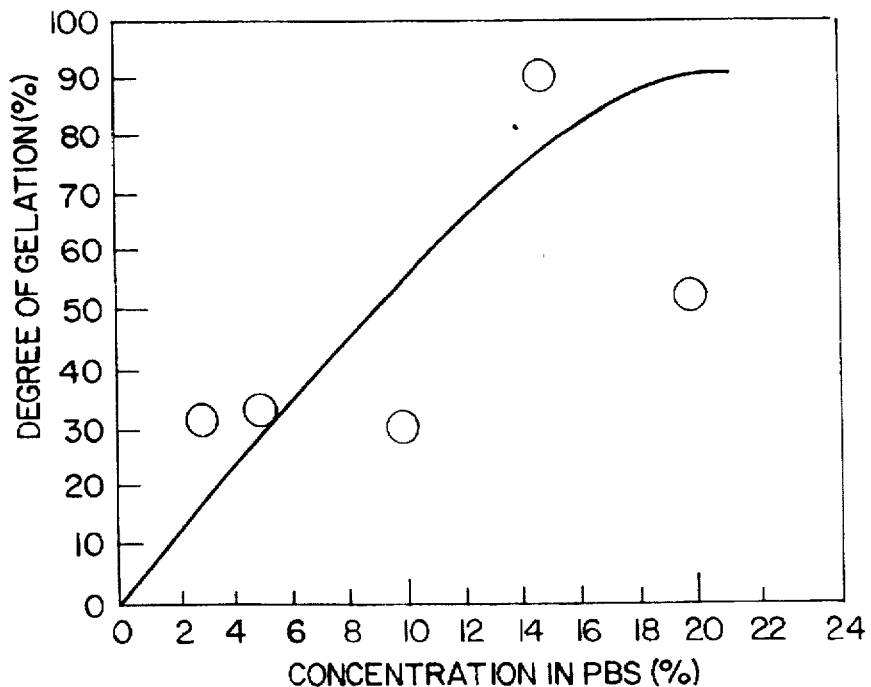
FIG. 6 graphically shows the dependency of the degree of gelation (%) in photocuring of chondroitin sulfate-cinnamic acid ester (lot CS-Cin-2) on its concentration in its PBS solution.

The lot CS-Cin-2 (DS=0.51) was dissolved in phosphate buffered saline (PBS) in various concentrations and the solutions were irradiated with light for 30 minutes and then examined for degree of gelation. The results thus obtained are shown in FIG. 6. As shown in FIG. 6, the degree of gelation increased with the increase in concentration.

The degree of gelation (%) was calculated as follows:

Percent gelation (%)=100×(A−X)/(A−B)

where A=the absorbance ($OD_{275\ nm}$) before irradiation,

B=the absorbance ($OD_{275\ nm}$) obtained after sufficient irradiation for the absorbance to arrive at a constant level, and X=the absorbance ($OD_{275\ nm}$) after 30 minutes of irradiation.

Figure 7:
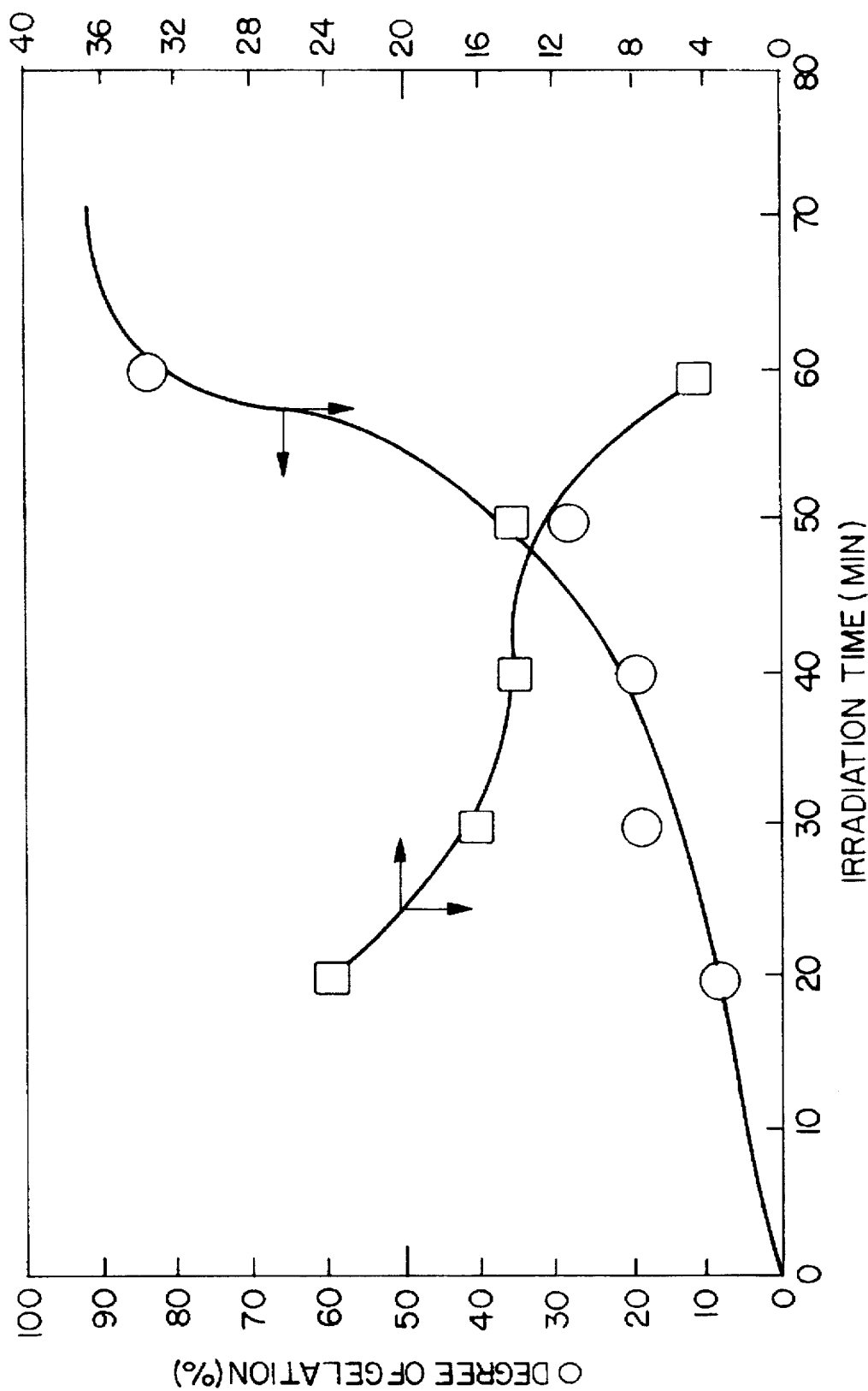
FIG. 7 graphically shows the dependency of the degree of gelation (%) in crosslinked chondroitin sulfate gel formation and of the swelling capacity on the time of exposure of chondroitin sulfate-cinnamic acid ester (lot CS-Cin-3) in PBS to light.

A 15% solution of the lot CS-Cin-3 (DS=0.65) in PBS was irradiated with light and the state of gelation was followed as a function of time. Thus, after each exposure period, the gel formed was immersed in deionized water for 24 hours, and weighed after removing the moisture on the gel surface. The gel was then dried, and the swelling capacity was calculated. The degree of gelation was also determined. The results thus obtained are shown in FIG. 7.

The degree of gelation increased and the swelling capacity decreased as the exposure period was prolonged.

Figure 8:
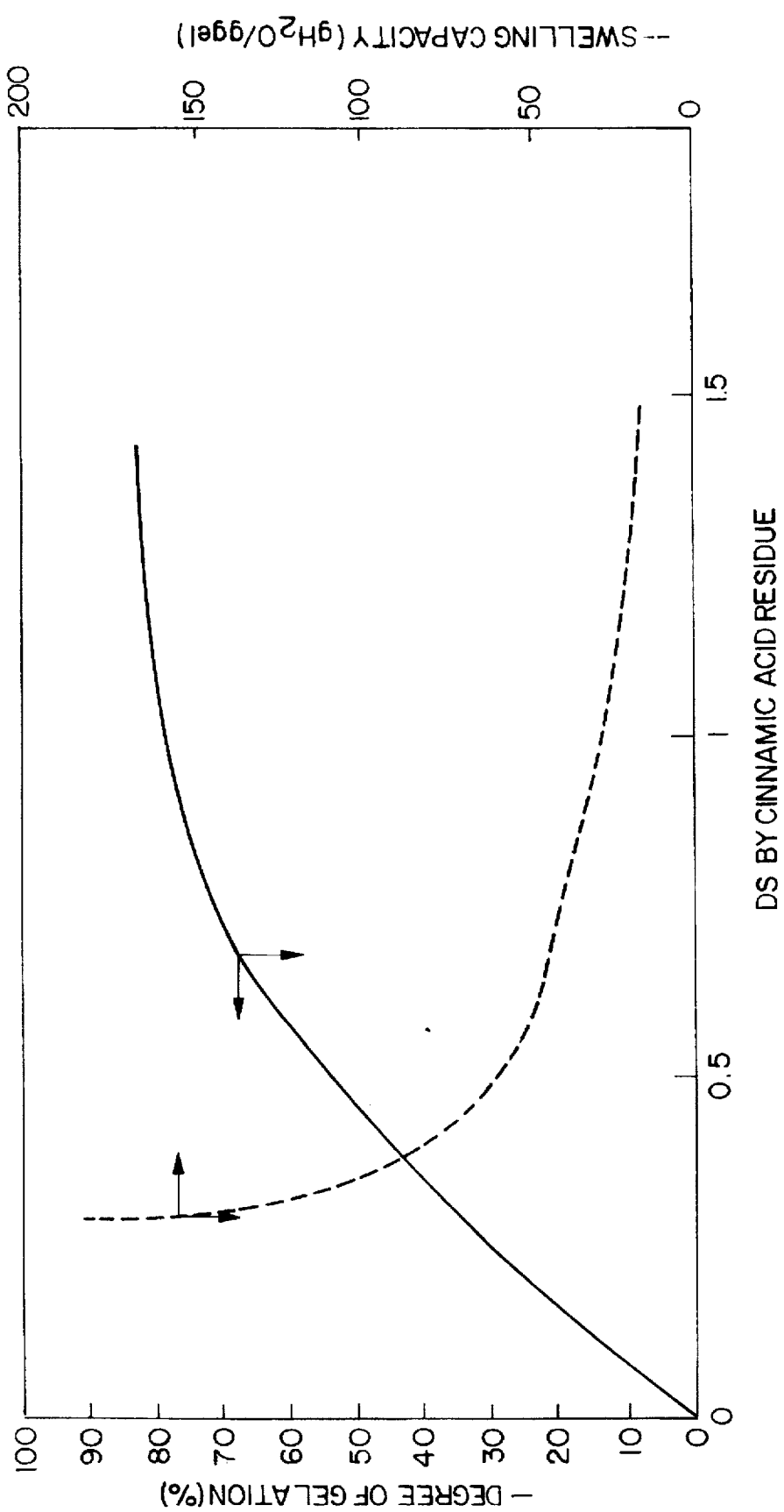
FIG. 8 graphically shows the dependency of the degree of gelation (%) in crosslinked chondroitin sulfate gel formation and of the swelling capacity on the DS by the cinnamic acid residue.

The lots CS-Cin-1 to 5 were also evaluated for their gelation behavior in PBS, and the resulting gels for swelling capacity. The relationship thus found between the degree of gelation or swelling capacity and the DS of cinnamic acid residue (mole ratio relative to chondroitin sulfate-constituting disaccharide unit) is shown in FIG. 8.

An increase in DS of cinnamic acid residue resulted in an increased degree of gelation, with a rapid decrease in swelling capacity.

EXAMPLE 8

Swelling capacity evaluation of cured (crosslinked) chondroitin sulfate films

The chondroitin sulfate-cinnamic acid esters synthesized in Examples 6 and 7 were molded into photocurable films, which were then irradiated with light for 30 minutes for crosslinking to give cured chondroitin sulfate films.

Figure 9:
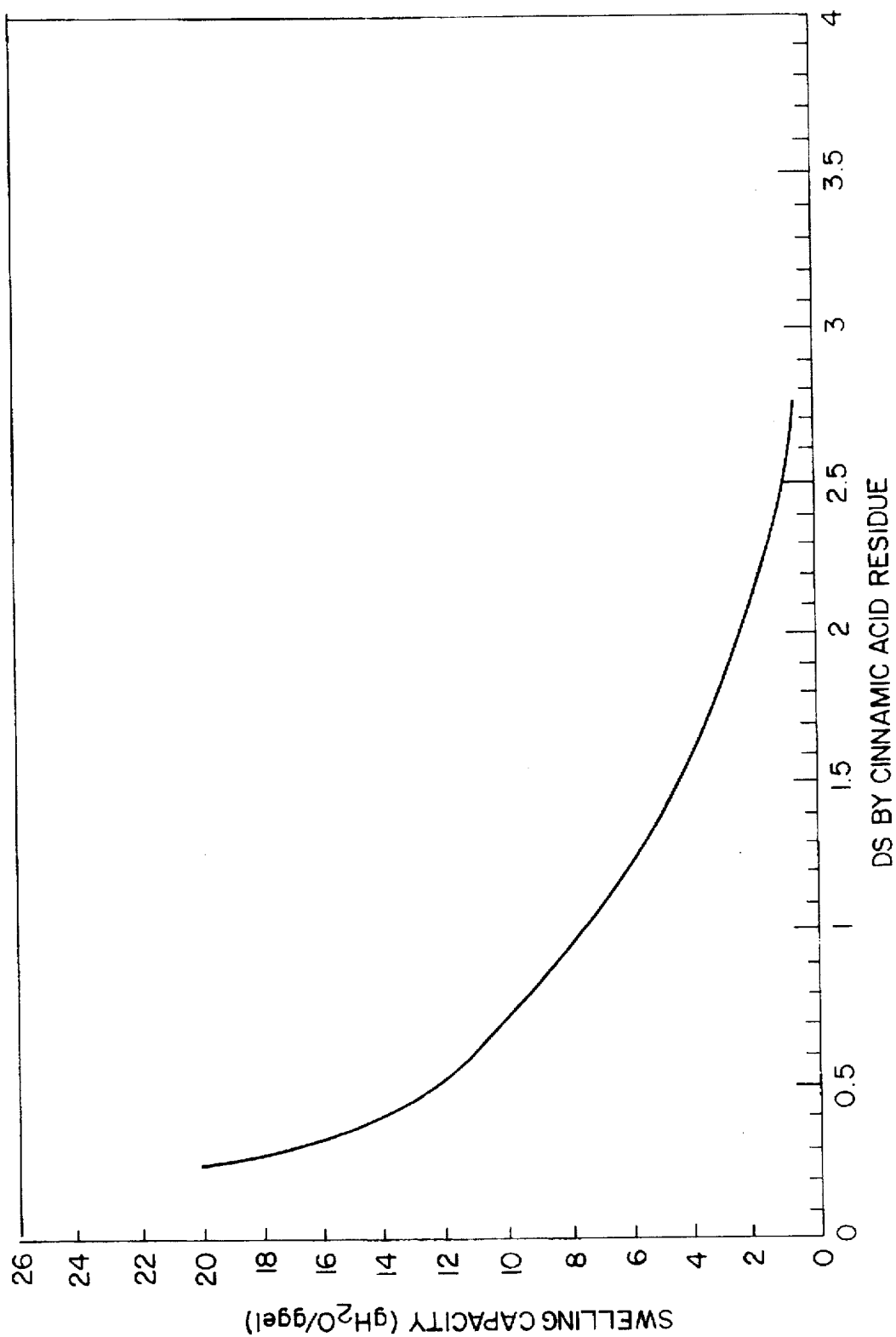
FIG. 9 graphically shows the dependency of the swelling capacity on the DS in crosslinked chondroitin sulfate films.

These cured chondroitin sulfate films were measured for swelling capacity. The results are shown in FIG. 9.

The results indicated that, unlike the cured hyaluronic acid films, the cured chondroitin sulfate films do not show such a rapid decrease in swelling capacity as found with the cured hyaluronic acid films even when the DS of the cinnamic acid residue is increased. This is presumably due to the fact that the cured chondroitin sulfate films have sulfate groups and are higher in hydrophilicity than the cured hyaluronic acid films.

EXAMPLE 9

Figure 10:
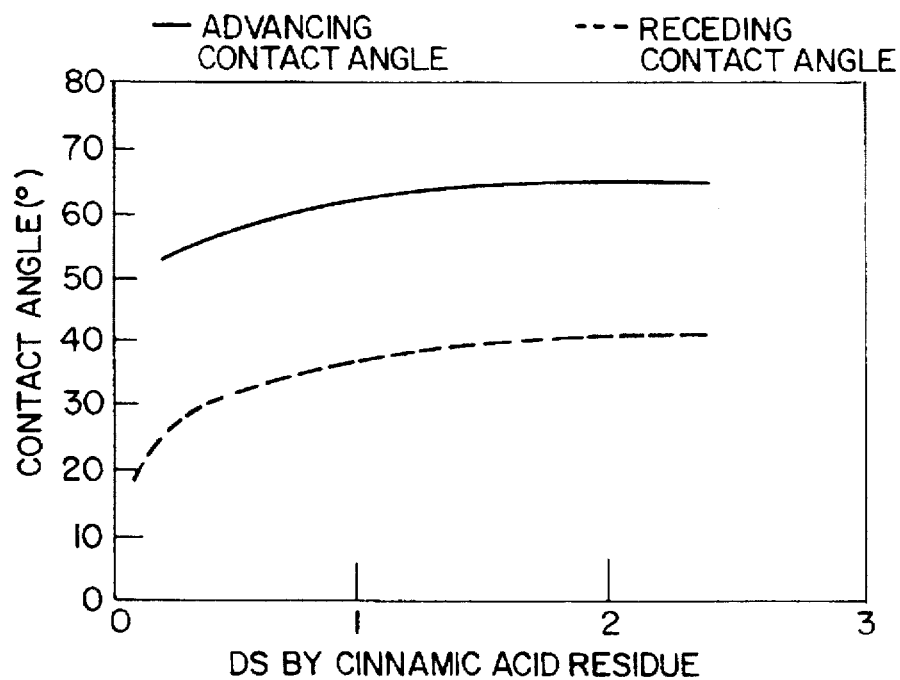
FIG. 10 graphically shows the dependency of the contact angle on the DS by the cinnamic acid residue in crosslinked chondroitin sulfate films obtained in Example 8.

The contact angles of the cured (crosslinked) chondroitin sulfate films obtained in Example 8 were measured and plotted against the DS of the cinnamic acid residue. The results are shown in FIG. 10. The graphic representation in FIG. 10 indicates that the crosslinked chondroitin sulfates show smaller contact angles as compared with the crosslinked hyaluronic acids. This is also presumably due to the difference in hydrophilicity.

EXAMPLE 10

Adhesion of Endothelial Cells to Cured (crosslinked) Chondroitin Sulfate Films

The adhesion of endothelial cells to the cured chondroitin sulfate films obtained in Example 8 was examined in the same manner as in Example 5. Unlike the cured hyaluronic acid films, no adhesion was observed irrespective of DS of cinnamic acid residue.

EXAMPLE 11

Binding of Cinnamic Acid Derivative to Carboxyl Groups of Hyaluronic Acid and Crosslinking (1) Synthesis of cinnamoyl ethylenediamine amide Cinnamoyl chloride (1.666 g) was dissolved in 100 ml of chloroform, and 6 g of ethylenediamine in chloroform was added dropwise to the solution at 0° C. After 20 hours of stirring at 40° C., the reaction mixture was washed with a saturated sodium hydrogen carbonate solution and then thoroughly washed with water. The organic solvent layer was concentrated under reduced pressure and the residue was recrystallized from ethanol to give the desired product (1.58 g; hereinafter referred to as compound A).

(2) Synthesis of Nα-Cinnamoyl-L-lysine

Ne-t-Butoxycarbonyl-L-lysine (2.58 g) was dissolved in 50 ml of dimethylformamide, and 30 ml of anhydrous pyridine was added to the solution. To the mixture was added a solution of cinnamoyl chloride in chloroform (1.665 g/20 ml) was added, and the reaction was carried out at 40° C. The reaction mixture was concentrated to dryness under reduced pressure, the residue was dissolved in 3.6N HCl/ dioxane (33 ml) and, after 4 hours of standing, the solution was concentrated under reduced pressure to give the desired compound (2.43 g; hereinafter referred to as compound B).

(3) Binding of Cinnamoyl Ethylenediamine Amide to Hyaluronic Acid

In 30 ml of water was dissolved 150 mg of sodium hyaluronate (mol. wt.=1,200,000), followed by addition of 42.75 mg of compound A and 71.9 mg of 1-ethyl-3-(3-dimethylaminopropyl)carbodiimide hydrochloride. The reaction was carried out at room temperature for 20 hours. To the reaction mixture was added 1M aqueous sodium hydrogen carbonate and, after standing at room temperature for 1 hour, sodium acetate-saturated ethanol was added. The resulting white precipitate was collected and thoroughly washed with ethanol.

| Lot: | HA—CinA-1 |
|---|---|
| Yield: | 176.2 mg |
| Bound compound A: | 16.58 wt. % |
| DS: | 0.5 |

(4) Binding of Nα-cinnamoyl-L-lysine to Hyaluronic Acid

To a solution of tri-n-butylamine salt of hyaluronic acid (mol. wt.=880,000) in dimethylformamide (150 mg/35 ml) were added 1.224 g of N-hydroxysuccinimide and 55 mg of dicylohexylcarbodiimide, and the reaction was carried out first at 0° C. for 1 hour and then at room temperature for 10 hours, for activating the carboxyl group of hyaluronic acid. Ether was added to the reaction mixture and the resulting precipitate was collected, washed with ether and dried under reduced pressure to give the corresponding activated hyaluronic acid ester.

This activated hyaluronic acid was dissolved in dimethylformamide. To this solution was added a solution of compound B in dimethylformamide (44 mg/50 ml), and the reaction was carried out at room temperature for 20 hours. Sodium acetate-saturated ethanol was added to the reaction mixture and the resulting precipitate was filtered off and purified by washing with ethanol.

| Lot: | HA—CinB-1 |
|---|---|
| Yield: | 122.1 mg |
| Bound compound B: | 25.92 wt. % |
| DS: | 0.5 |

(5) Preparation of Cured (crosslinked) Hyaluronic Acid Films

The lots HA-CinA-1 and HA-CinB-1 (30 mg each) were molded into films in the same manner as in Example 1 and crosslinked by irradiation with light.

The thus-prepared cured hyaluronic acid films (lots: HA-CinA-1-2 and HA-CinB-1-2, respectively) showed swelling capacity values of 1.2 and 1.4 g $H_2O$/g gel, respectively.

EXAMPLE 12

Synthesis of Hyaluronic Acid-[1-(2-carboxyethyl) thymine] ester (1)

To a solution of hyaluronic acid (mol. wt. 1,000,000) (hereinafter referred to as HA100) in dimethylformamide (DMF) (175 mg/50 ml) containing 0.317 g of 2-chloro-1-methylpyridinium iodide were added 0.245 g of 1-(2-carboxyethyl)thymine and 0.461 g of triethylamine, and the reaction was carried out at 90° C. for 4 hours. The DMF was removed under reduced pressure, an excess amount of ethanol was added, and the resulting precipitate was collected, washed with ethanol and dried under reduced pressure. The white precipitate obtained is the hyaluronic acid-[1-(2-carboxyethyl)thymine] ester.

| Lot: | HA—Thym-1 |
|---|---|
| Yield: | 160.0 mg |
| Bound thymine: | 9.1 wt. % |
| DS: | 0.46 |

(The DS was determined based on the ratio between the number of methyl protons of thymine and the number of acetyl protons of hyaluronic acid as determined by $^1$H NMR.)

EXAMPLE 13

Synthesis of Hyaluronic Acid-[1-(2-carboxyethyl) thymine] ester (2)

Several lots of hyaluronic acid-[1-(2-carboxyethyl)-thymine] ester were prepared in the same manner as in Example 12 except that the conditions specified in Table 3 were used.

TABLE 3

| | Reaction conditions | | | | Physical characteristics | |
|---|---|---|---|---|---|---|
| | Thymine/HA | Temper- | | | Solubility (mg/ml) | |
| Lot | OH mole ratio | ature (°C.) | Time (hrs) | DS | Water | DMF |
| HA-Thym-2 | 0.5/1.0 | 90 | 3 | 0.05 | 1 | 20 |
| 3 | 1.0/1.0 | 75 | 2 | 0.125 | 10 | 80 |
| 4 | 2.0/1.0 | 75 | 2 | 0.14 | 10 | 80 |
| 5 | 0.67/1.0 | 90 | 4 | 0.17 | 50 | 80 |
| 6 | 1.0/1.0 | 90 | 3 | 0.26 | 20 | 80 |
| 7 | 1.0/1.0 | 90 | 6 | 0.35 | 20 | 80 |
| 8 | 0.67/1.0 | 100 | 4 | 0.37 | 50 | 80 |
| 9 | 3.0/1.0 | 90 | 3 | 2.40 | 0 | 100 |

EXAMPLE 14

Preparation of crosslinked hyaluronic acid by photoreaction of hyaluronic acid-[1-(2-carboxyethyl)thymine] ester (1)

Figure 11:
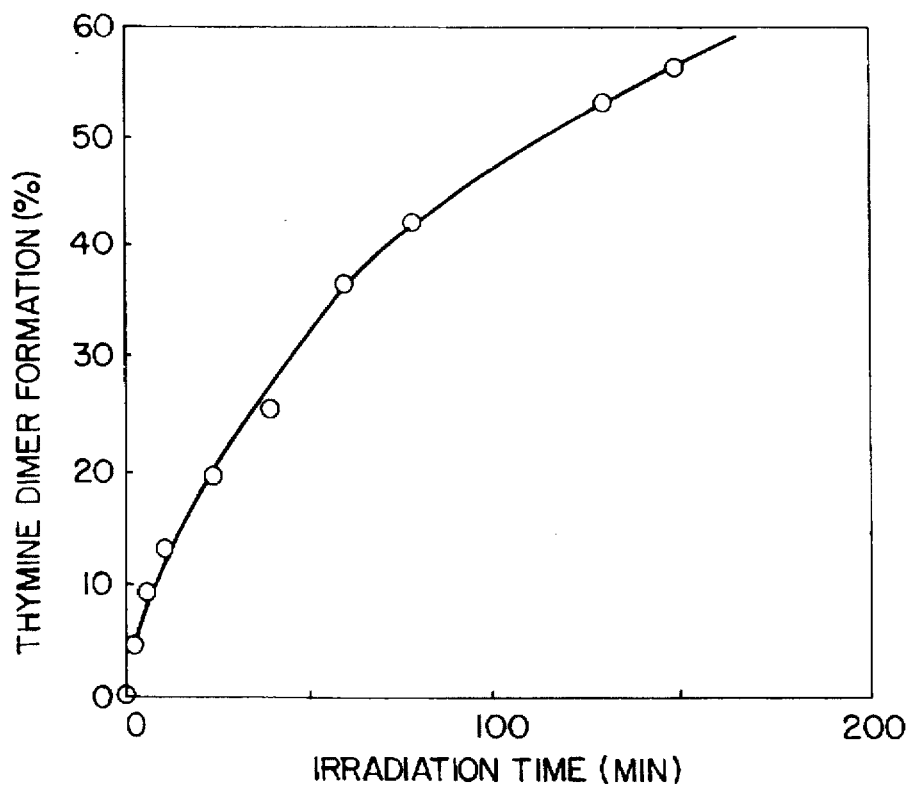
FIG. 11 graphically shows the dependency of the thymine dimer formation percentage on the time of UV (ultraviolet) irradiation in the process of crosslinked hyaluronic acid film formation by exposure of HA-Thym-1 to UV rays in Example 14.

A film was prepared from the lot HA-Thym-1 (DS=0.46) in the same manner as in Example 1 and irradiated with ultraviolet (UV) rays from a xenon lamp. The course of thymine dimer formation as found as a function of exposure time is shown in FIG. 11.

EXAMPLE 15

Preparation of cured (crosslinked) hyaluronic acid films by photocuring (photoreaction) of hyaluronic acid-[1-(2-carboxyethyl)thymine] esters (2)

The lots HA-Thym-3, 4, 6, 7, 8 and 9 (DS=0.125, 0.14, 0.26, 0.35, 0.37 and 2.40, respectively) prepared in Example 13 were respectively molded into films in the same manner as in Example 1 and the films were irradiated with UV using a xenon lamp. The thus-obtained cured hyaluronic acid films were designated as lots HA-Thym-3-2, 4-2, 6-2, 7-2, 8-2 and 9-2, respectively. The degree of gelation (%) and swelling capacity data for these films were as shown below in Table 4.

TABLE 4

| Lot | Degree of gelation (%) | Swelling capacity |
| --- | --- | --- |
| HA—Thym- 3-2 | 75.39 | 34.76 |
| 4-2 | 74.5 | 45.00 |
| 6-2 | 88.9 | 32.63 |
| 7-2 | 94.0 | 40.17 |
| 8-2 | 99.4 | 32.17 |
| 9-2 | 98.0 | 0.56 |

Synthesis of Hyaluronic Acid-[1-(2-carboxyethyl) thymine] esters (3)

A solution of hyaluronic acid in DMF (1.0 mM), after preliminary dried over molecular sieves, was thoroughly dehydrated by further 4 hours of deaeration. Separately, a DMF solution containing 1-(2-carboxyethyl)thymine (in varied mole ratio relative to each hydroxyl group of hyaluronic acid; cf. FIG. 12), 2-chloro-1-methylpyridinium iodide (1.2 mM) and triethylamine (1.2 mM) was stirred at room temperature for 30 minutes. This solution was added dropwise to the above-mentioned hyaluronic acid solution supplemented with triethylamine (1.2 mM). The resulting mixture was stirred at 90° C. for 3, 5 or 8 hours. The reaction mixture was concentrated under reduced pressure and methanol was added to the residue. The resulting precipitate was filtered off, washed with methanol and dried. In this manner, hyaluronic acid-[1-(2-carboxyethyl)thymine] esters differing in DS were obtained (HA-Thym; DS=0.2, 0.4, 0.6, 0.7, 0.9, 1.3, 1.8, 2.2).

Figure 12:
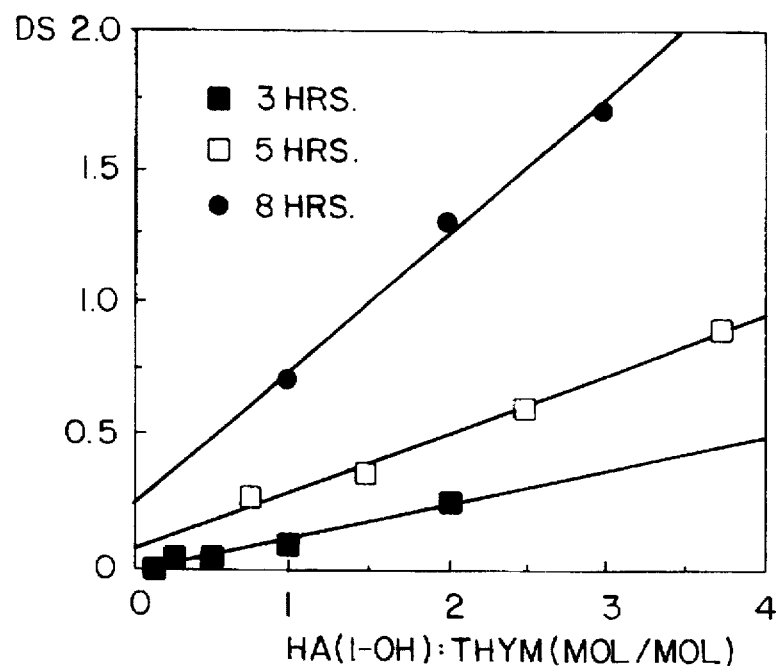
FIG. 12 graphically shows the relationship between the 1-(2-carboxyethyl)thymine/HA mole ratio and the DS in the HA-Thym synthesis in Example 16.

An example of the relationship between the mole ratio of 1-(2-carboxyethyl)thymine as used and the DS is shown in FIG. 12.

EXAMPLE 17

Synthesis of Chondroitin Sulfate-[1-(2-carboxyethyl)-thymine] Esters

The procedure of Example 16 was followed except that chondroitin sulfate (mol. wt.=60,000) was used, with the mole ratio of 1-(2-carboxyethyl)thymine varied relative to each hydroxyl group of chondroitin sulfate and that the esterification reaction was 3, 5 or 9 hours. Methanol or diethyl ether was added to each reaction mixture for precipitation of the product. When diethyl ether was used, the precipitate was thoroughly washed with methanol. In this way, chondroitin sulfate-[1-(2-carboxyethyl)thymine] esters differing in DS were obtained (CS-Thym; DS=0.09, 0.4, 0.8, 0.9, 1.3, 1.7, 1.8, 2.2).

Figure 13:
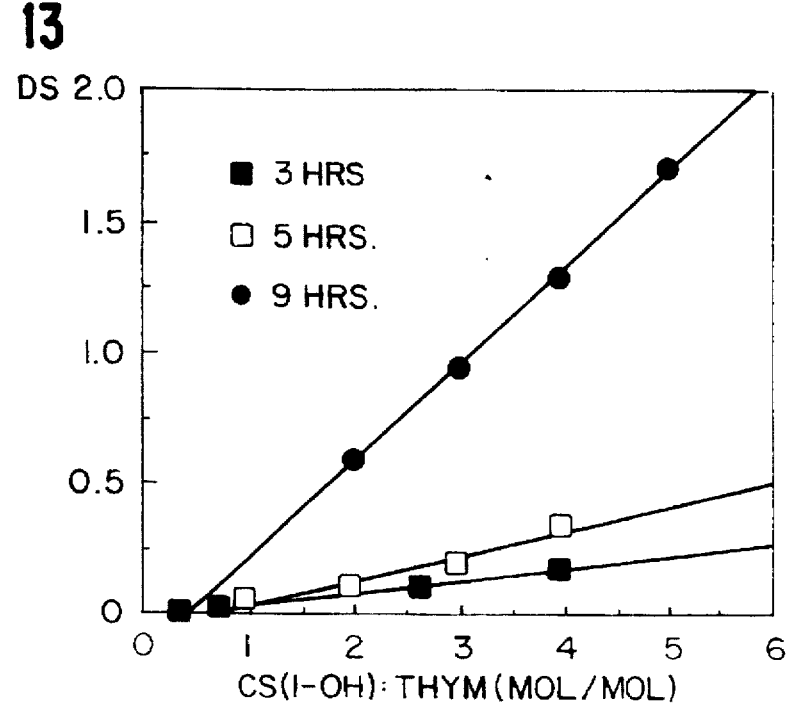
FIG. 13 graphically shows the relationship between the 1-(2-carboxyethyl)thymine/CS mole ratio and the DS in the CS-Thym synthesis in Example 17.

An example of the relationship between the mole ratio of 1-(2-carboxyethyl)thymine as used and the DS is shown in FIG. 13.

The DS-solubility (in water or DMF) relationship is shown in Table 5.

TABLE 5

| | Solubility | |
| DS | Water | DMF |
| --- | --- | --- |
| 0.4 | Soluble | Soluble |
| 0.9 | Soluble | Soluble |
| 1.3 | Sparingly soluble | Soluble |
| 1.7 | Insoluble | Soluble |

EXAMPLE 18

Preparation of Cured (crosslinked) Hyaluronic Acid Films and Cured (crosslinked) Chondroitin Sulfate Films Using Thymine Derivative The above films were prepared using the 1-(2-carboxyethyl)thymine esters of each GAG as obtained in Example 16 or 17.

Thus, each of the hyaluronic acid-[1-(2-carboxyethyl) thymine] esters (HA-Thym; DS=0.2, 0.4, 0.6, 0.7, 0.9, 1.3, 1.8, 2.2) and chondroitin sulfate-[1-(2-carboxyethyl) thymine] esters (CS-Thym; DS=0.09, 0.4, 0.8, 0.9, 1.3, 1.7, 1.8, 2.2) was dissolved in DMF to give a 5% solution, and 200 µl of the solution was placed on a slide glass (14 mm in diameter) and dried using sterile air at 35° C. The resulting film was irradiated with rays from a 400 W high pressure mercury lamp through a pyrex-water filter to give a crosslinked GAG film.

Figure 14:
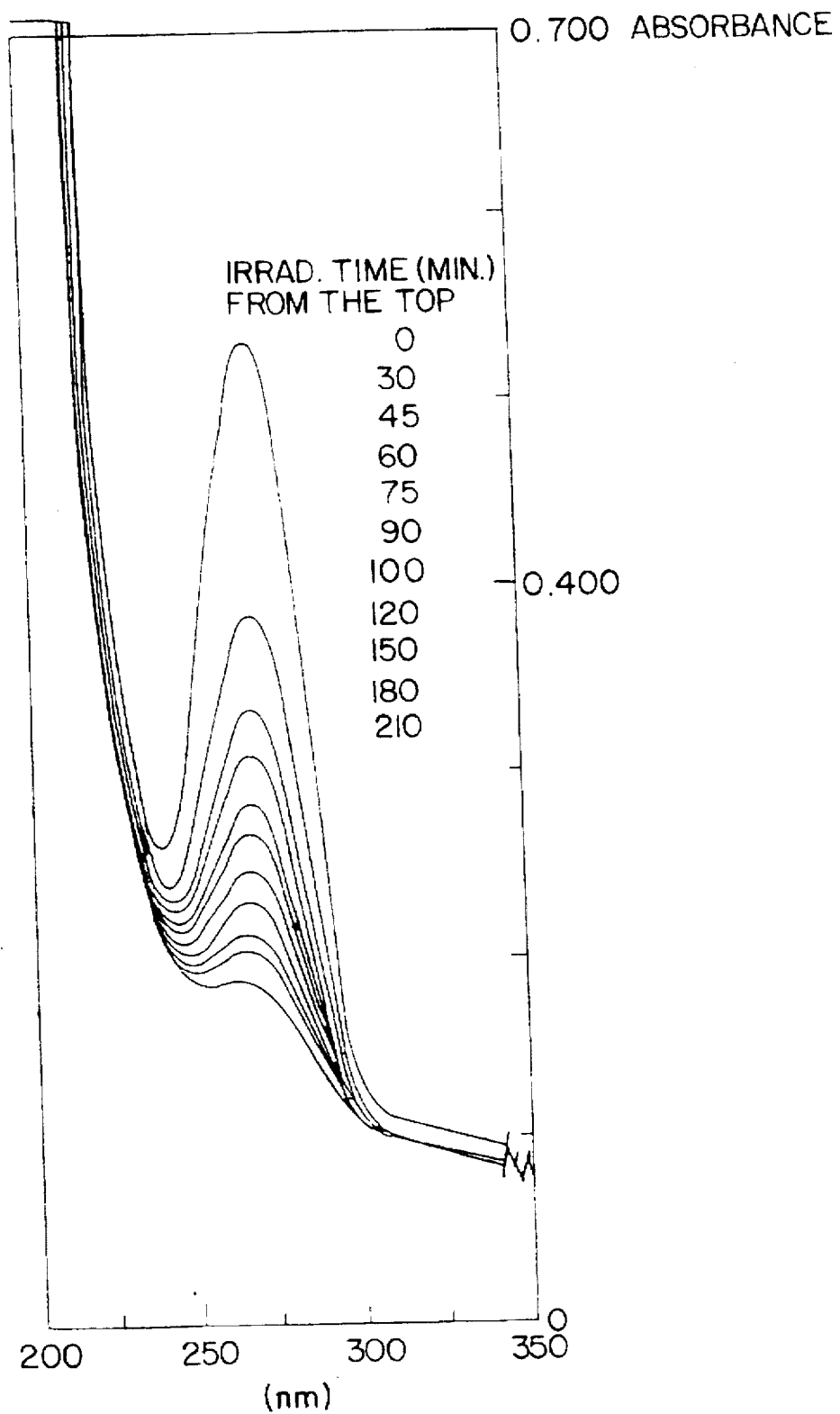
FIG. 14 graphically shows the relationship between the change in the absorption (at 270 nm) of thymine and the irradiation time in the exposure of thin CS-Thym films to light in Example 18.
Figure 15:
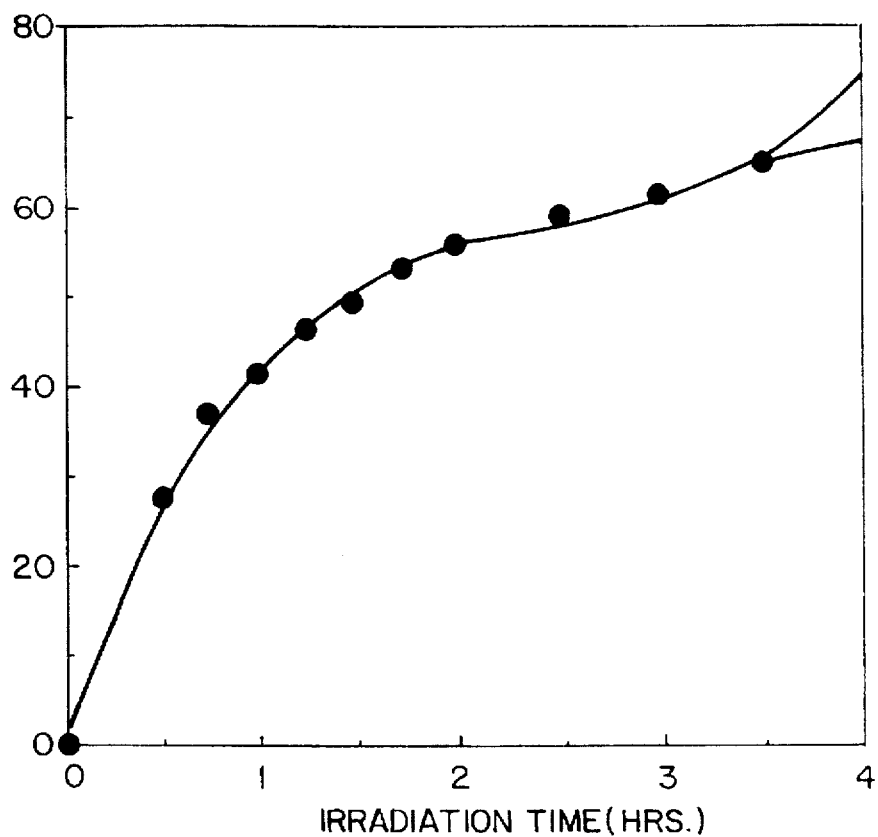
FIG. 15 graphically shows the relationship between the degree of gelation (%) and the irradiation time in the exposure of a thin CS-Thym film to light in Example 18.
Figure 16:
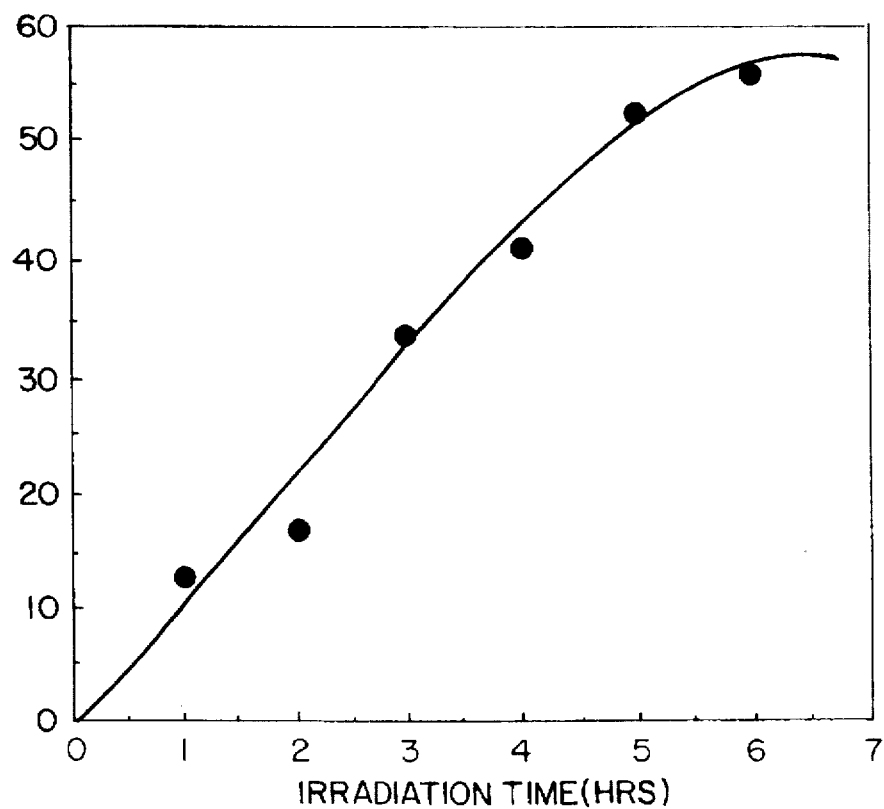
FIG. 16 graphically shows the relationship between the degree of gelation (%) and the irradiation time in the exposure of another thin CS-Thym film to light in Example 18.

The relationship between the change in absorption (270 nm) and the exposure time as found when dried thin chondroitin sulfate-[1-(2-carboxyethyl)thymine] ester (CS-Thym), films (DS=0.09, thickness=2–3 µm) were irradiated in the above manner is shown in FIG. 14. The relationship between degree of gelation (%) and exposure time as found on that occasion is shown in FIG. 15. Films of a CS-Thym (DS=0.09) having a thickness suited for practical use (10–12 µm) were also irradiated in the same manner; the relationship between degree of gelation (%) and exposure time was as shown in FIG. 16.

Figure 17:
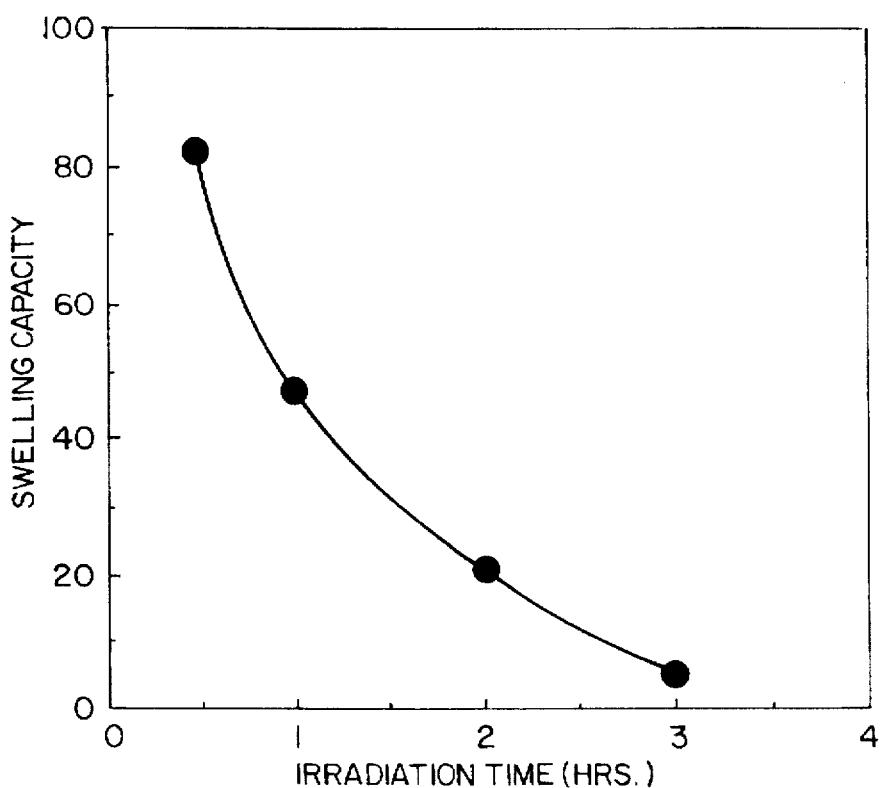
FIG. 17 graphically shows the relationship between the swelling capacity and the irradiation time in the exposure of EL thin HA-Thym film to light in Example 18.
Figure 18:
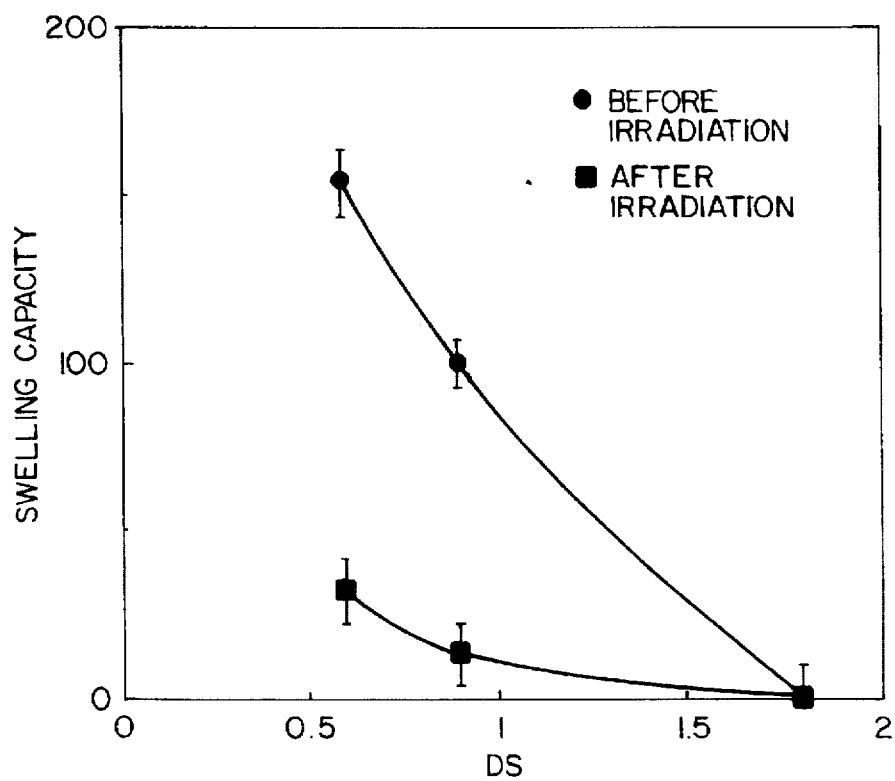
FIG. 18 graphically shows the relationship between the swelling capacity and the DS for thin HA-Thym films before and after the exposure to light in Example 18.

Dried hyaluronic acid-[1-(2-carboxyethyl)thymine) ester (HA-Thym) films (DS=0.9, thickness=10–12 µm) were irradiated in the same manner, giving the swelling capacity-exposure time relationship shown in FIG. 17. IA-Thym films differing in DS were each measured for swelling capacity before and after irradiation (3 hours) and the data were plotted against the DS, giving the curves shown in FIG. 18.

The contact angle and swelling capacity data obtained for several of the HA-Thym- or CS-Thym-derived photocured (crosslinked) films obtained in this example and differing in DS are shown in Table 6.

TABLE 6

| Photocurable GAG | Contact angle (degrees) ± SD | Swelling capacity |
| --- | --- | --- |
| HA—Thym (0.6) | — | 32 ± 7 |
| HA—Thym (0.9) | — | 13 ± 4 |
| HA—Thym (1.3) | — | 7 |
| HA—Thym (1.8) | 54 ± 3 | 0 |
| CS—Thym (0.9) | — | 40 ± 13 |
| CS—Thym (1.3) | — | 22 ± 5 |
| CS—Thym (1.8) | — | |
| CS—Thym (2.2) | 70 ± 2 | 3 |

EXAMPLE 19

Adhesion of Endothelial Cells to the Crosslinked Hyaluronic Acid Film

Endothelial cells were grown on the crosslinked hyaluronic acid films (DS=0.4, 0.6, 1.3, 1.8) varying in DS as prepared with a thymine derivative in Example 18 and the degree of adhesion of the cells was evaluated 6 hours after the beginning of culture.

As a result, the adhesion, extension (spreading) and growth of endothelial cells were scarcely observed on any of the crosslinked hyaluronic acid films varying in DS. On the other hand, normal attachment, extension (spreading) and growth were found in the wells of the control TCPS.

EXAMPLE 20

Synthesis of Chondroitin Sulfate-(7-coumaryloxyacetic acid) Ester

Figure 19:
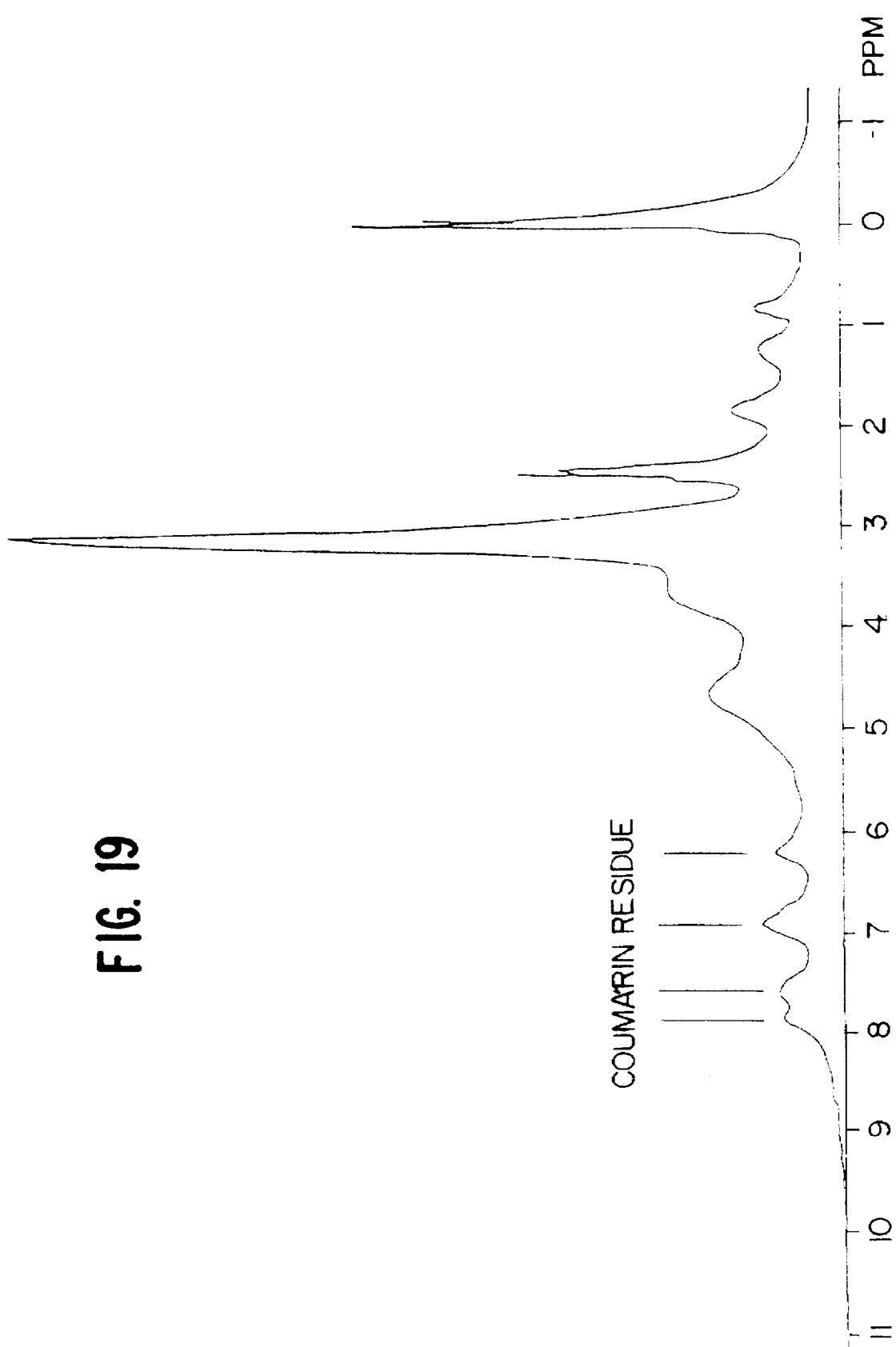
FIG. 19 shows a $^1$H NMR spectrum of the chondroitin sulfate-(7-coumaryloxy)acetic acid ester prepared in Example 20.

A solution of chondroitin sulfate tri-n-butylamine salt in DMF (10.25 mg/ml) was previously dried over molecular sieves and 70 ml of this solution was dried in vacuo with stirring in a 100 ml three-necked flask at room temperature. After the atmosphere was replaced with nitrogen gas, 15 ml of distilled pyridine was added. To this was added a solution of one mole equivalent, relative to each OH group of chondroitin sulfate, of 7-coumaryloxyacetyl chloride [acid chloride form coumarin] (1.12 g) in 5 ml of DMF. The reaction was carried out by refluxing the mixture in a nitrogen atmosphere at 80° C. for 3 hours. The reaction mixture was then concentrated and added dropwise to diethyl ether. The resulting precipitate was recovered, dissolved in deionized water and dialyzed against running water for 3 days. The dialyzate was lyophilized to provide chondroitin sulfate-(7-coumaryloxyacetic acid) ester as a white solid. Yield: 965.1 mg DS: 0.021 Swelling capacity: 2.8 g $H_2O$/g dry gel $^1$H-NMR spectrum: See FIG. 19

Figure 20:
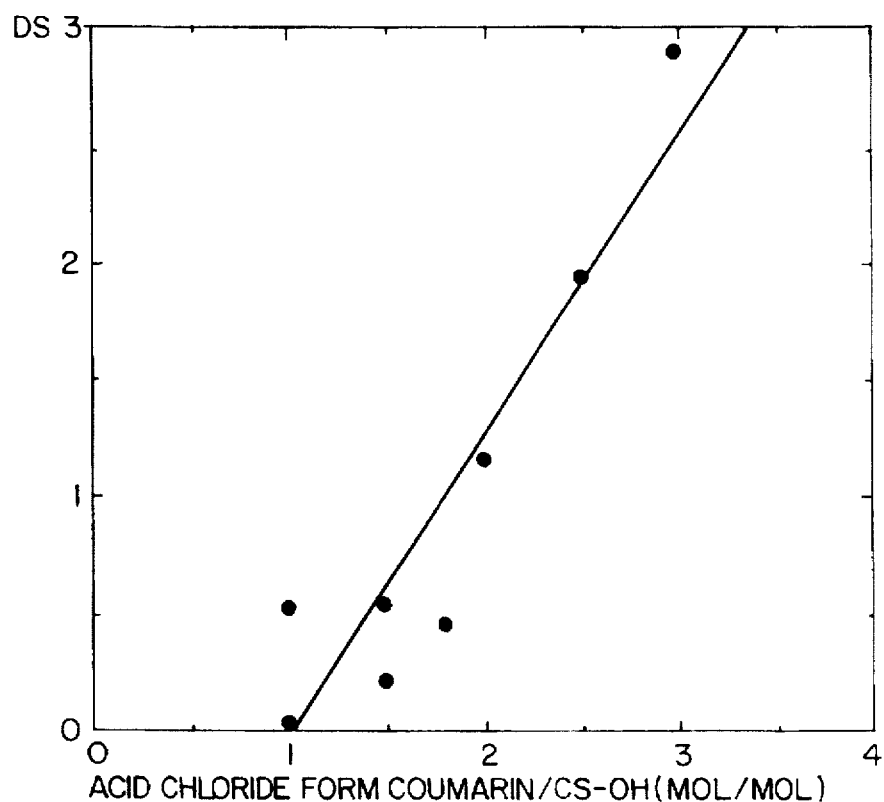
FIG. 20 graphically shows the relationship between the acid chloride form coumarin/chondroitin sulfate hydroxyl group (CS—OH) mole ratio and the DS in the ester formed.
Figure 28:
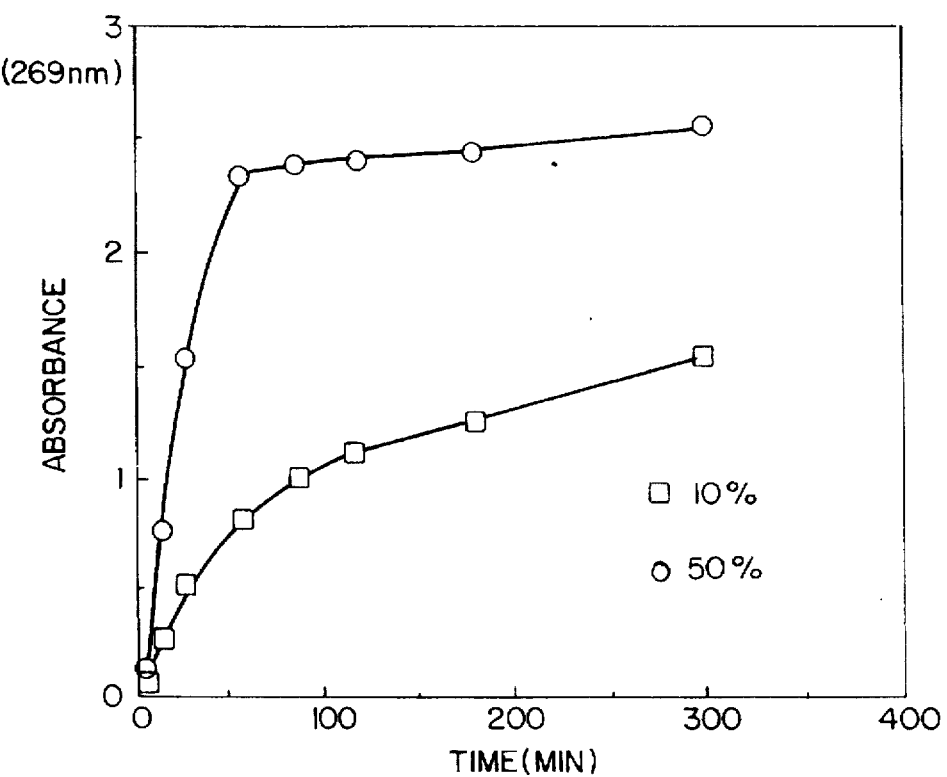
FIG. 28 graphically shows the rate of drug release from a photocrosslinked CS-Thym film (DS=0.8) with a drug content of 10% or 50% as determined in Example 28 as a function of time, said rate being expressed in terms of change in absorbance (at 269 nm).

The above procedure was repeated except that the mole ratio of acid chloride form coumarin to the hydroxyl groups of chondroitin sulfate was varied and the DS was plotted against the mole ratio. The results are shown in FIG. 20.

EXAMPLE 21

Preparation of Photocured (crosslinked) Chondroitin Sulfate Film from Chondroitin Sulfate-(7-coumaryloxyacetic acid) Ester The chondroitin sulfate-(7-coumaryloxyacetic acid) ester synthesized in Example 20 was processed into a dry film as in Example 1 and the film was irradiated with UV light (320 nm) to provide a photocured chondroitin sulfate film.

Figure 21:
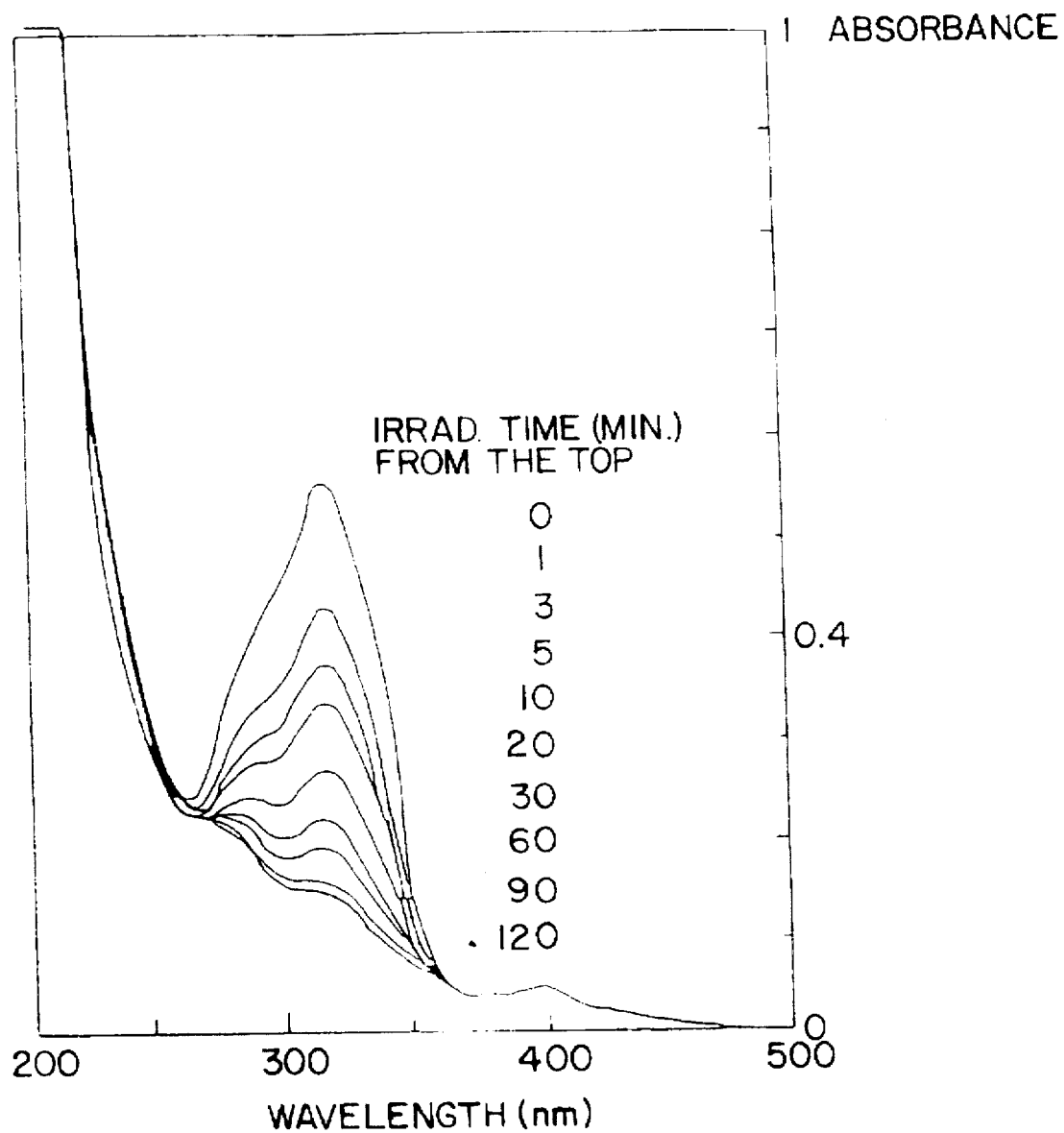
FIG. 21 graphically shows the relationship between the change in the absorption (at 320 nm) of coumarin and the irradiation time in the exposure of a thin chondroitin sulfate-(7-coumaryloxy)acetic acid ester film to light in Example 21.
Figure 22:
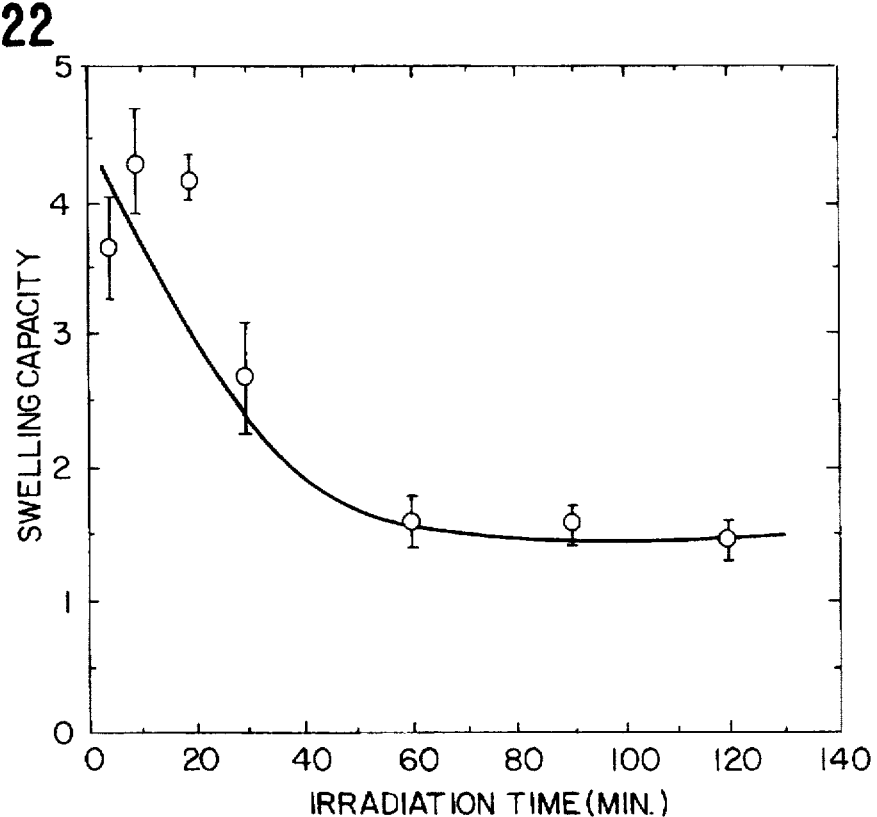
FIG. 22 graphically shows the relationship between the swelling capacity and the irradiation time in the exposure of thin chondroitin sulfate-(7-coumaryloxy)acetic acid ester films to light in Example 21.
Figure 23:
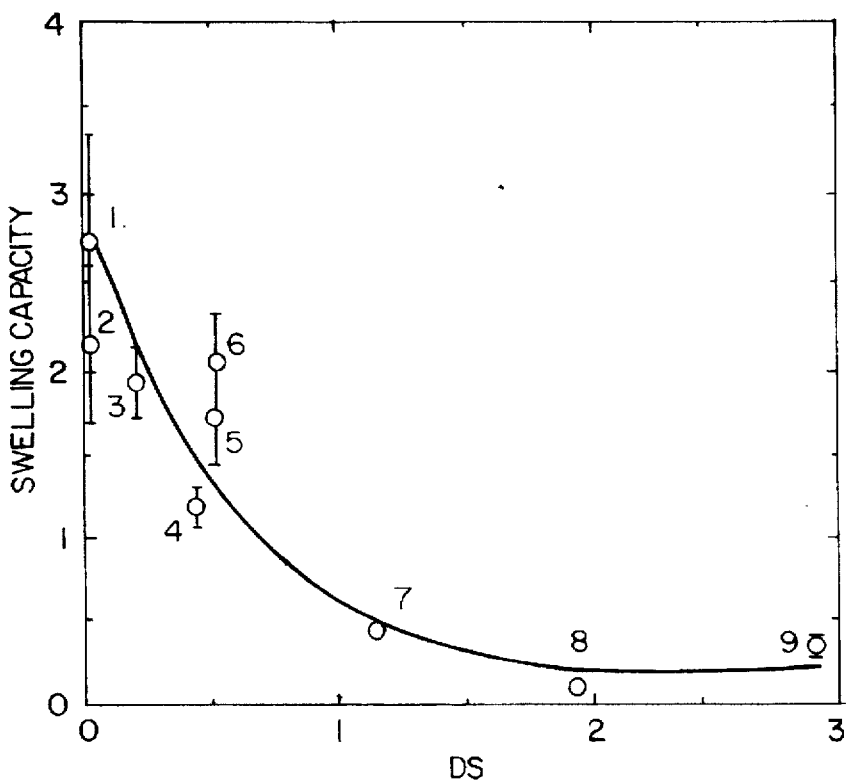
FIG. 23 graphically shows the relationship between the swelling capacity and the DS in the exposure of thin chondroitin sulfate-(7-coumaryloxy)acetic acid ester films to light in Example 21.
Figure 24:
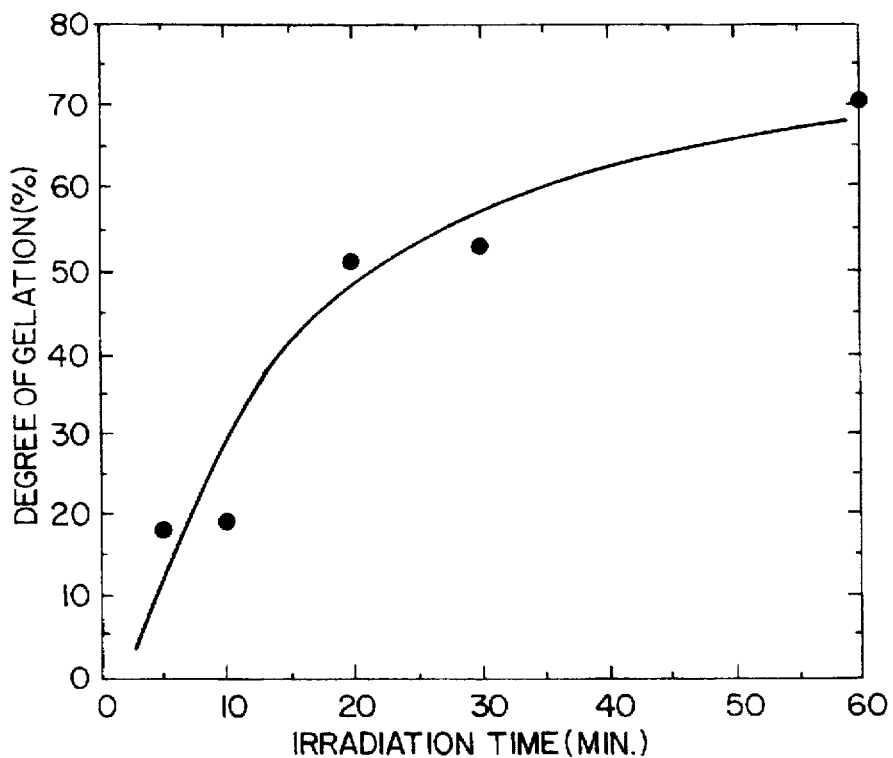
FIG. 24 graphically shows the relationship between the degree of gelation (%) and the irradiation time in the exposure of a thin chondroitin sulfalte-(7-coumaryloxy)acetic acid ester film to light in Example 21.
Figure 25:
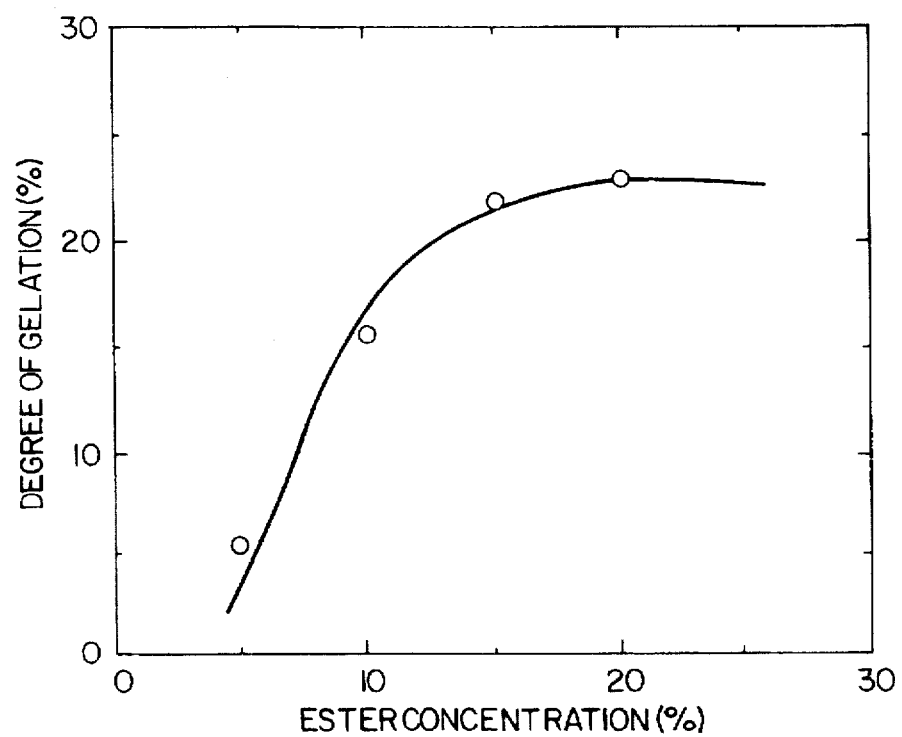
FIG. 25 graphically shows the relationship between the degree of gelation (%) and the concentration of chondroitin sulfate-(7-coumaryloxy)acetic acid ester in the exposure of thin films comprising said ester to light in Example 21.
Figure 26:
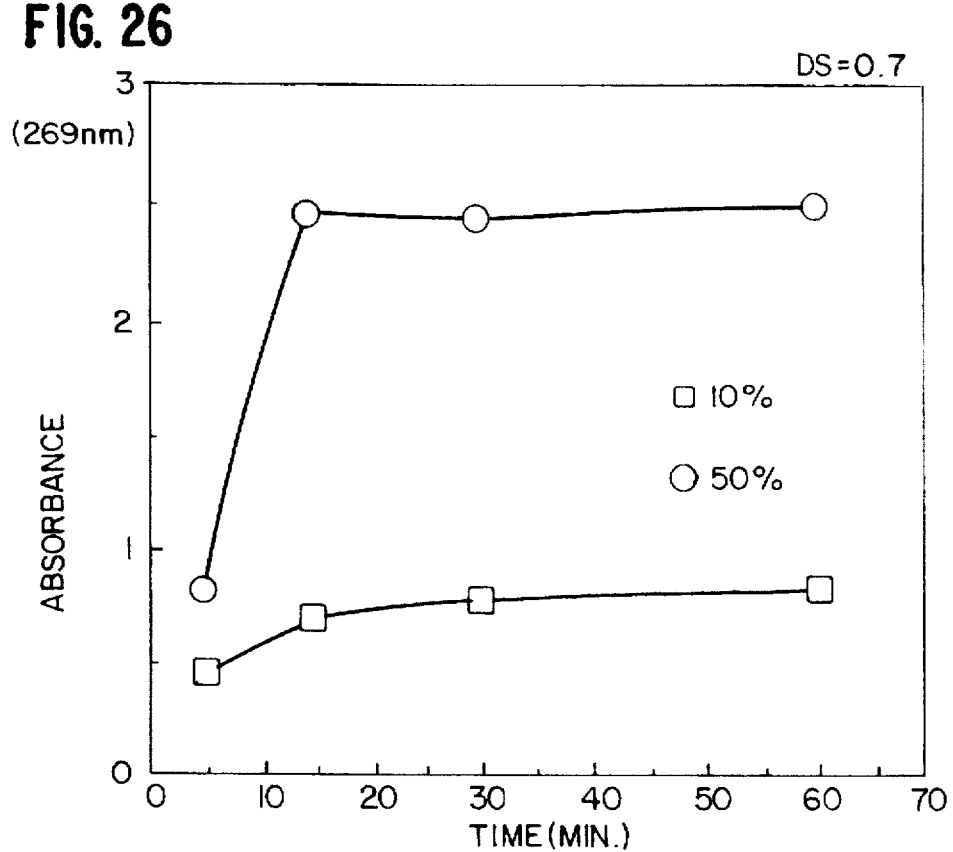
FIG. 26 graphically shows the rate of drug release from a photocrosslinked HA-Thym film (DS=0.7) with a drug content of 10% or 50% as determined in Example 28 as a function of time, said rate being expressed in terms of change in absorbance (at 269 nm).
Figure 27:
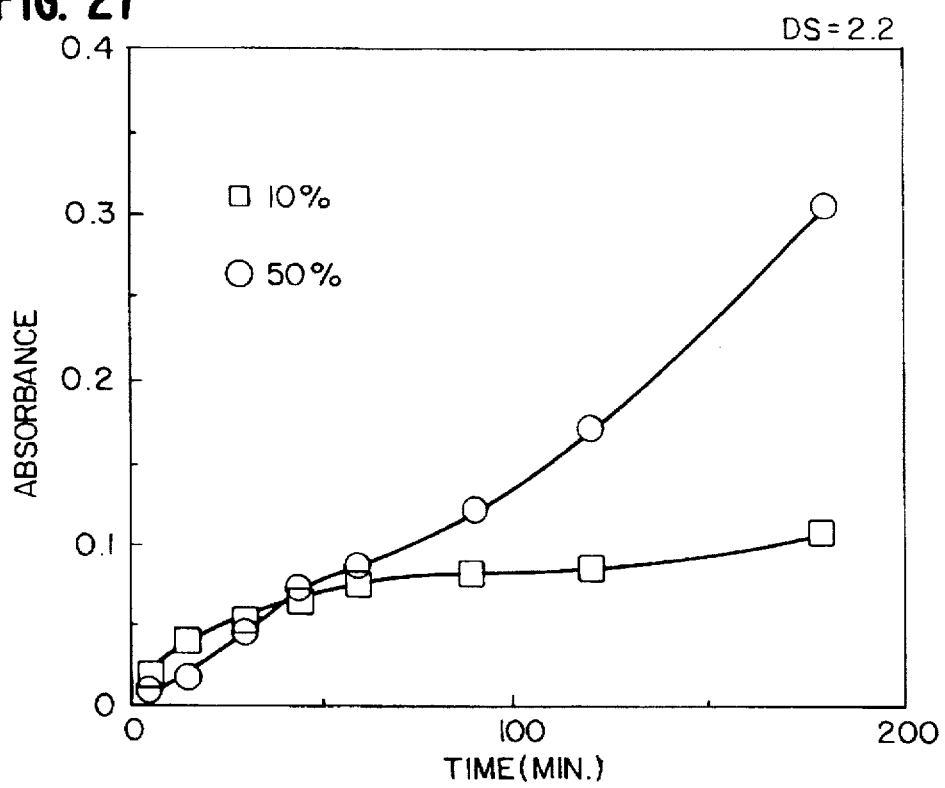
FIG. 27 graphically shows the rate of drug release from a photocrosslinked HA-Thym film (DS=2.2) with a drug content of 10% or 50% as determined in Example 28 as a function of time, said rate being expressed in terms of change in absorbance (at 269 nm).
Figure 29:
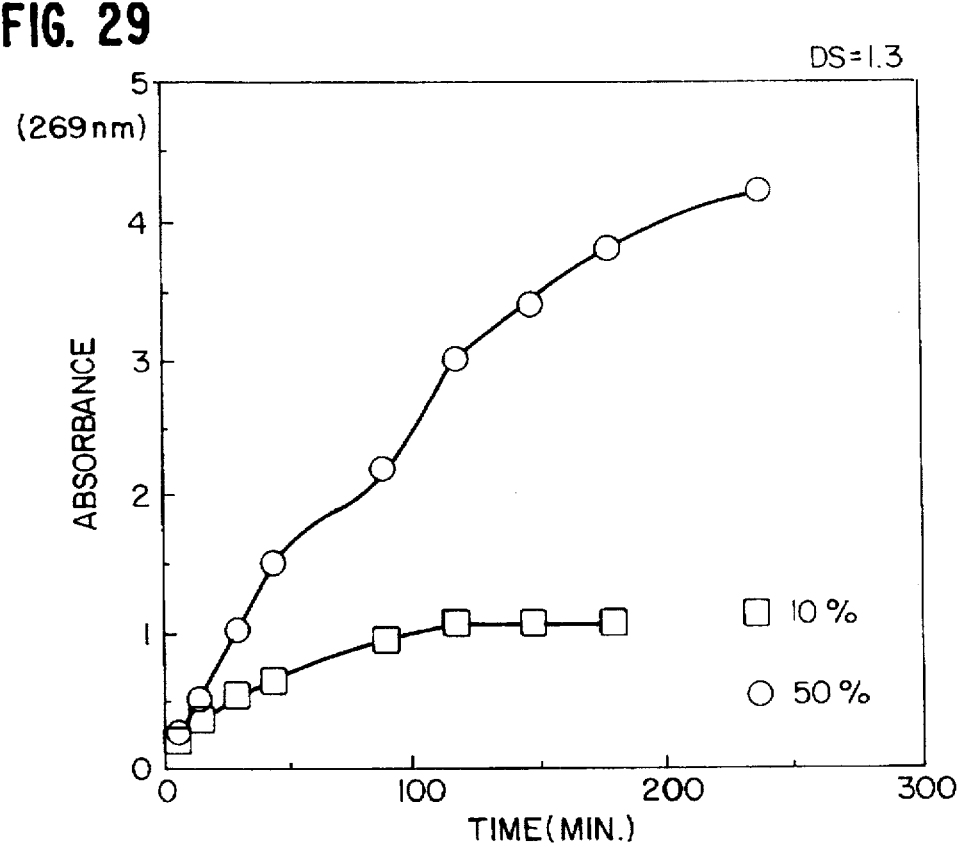
FIG. 29 graphically shows the rate of drug release from a photocrosslinked CS-Thym film (DS=1.3) with a drug content of 10% or 50% as determined in Example 28 as a function of time, said rate being expressed in terms of change in absorbance (at 269 nm).
Figure 30:
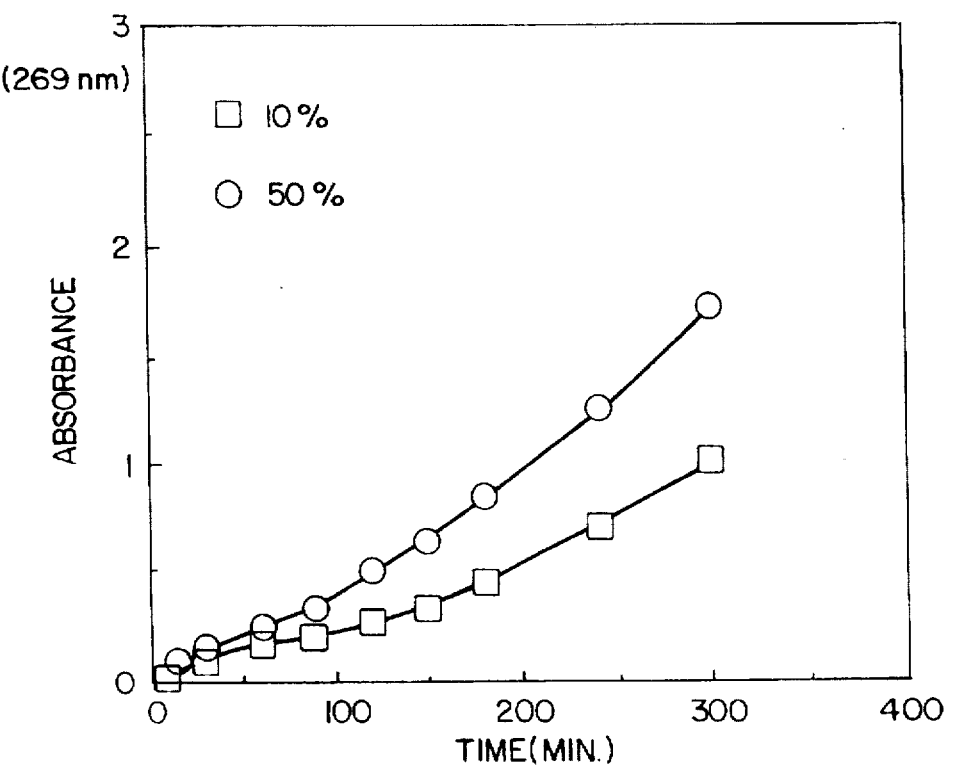
FIG. 30 graphically shows the rate of drug release from a photocrosslinked CS-Thym film (DS=1.8) with a drug content of 10% or 50% as determined in Example 28 as a function of time, said rate being expressed in terms of change in absorbance (at 269 nm).

The relationship between the exposure time and changes in the absorption spectrum (320 nm) of coumarin is shown in FIG. 21. The swelling capacity (g$H_2O$/g dry gel) of the film obtained was determined and plotted against exposure time and DS. The results are shown in FIGS. 22 and 23, respectively. In addition, the degree of gelation (%) was determined and plotted against the exposure time and the concentration of chondroitin sulfate-(7-coumaryloxyacetic acid) ester. The results are shown in FIGS. 24 and 25, respectively.

EXAMPLE 22

Crosslinked Hyaluronic Acid/chondroitin Sulfate Film

The HA-Cin-3(DS=0.5) obtained in Example 1 was dissolved in 20% aqueous solution of DMF at a final concentration of 5% by weight. Then, the CS-Cin-4(DS=1.37) obtained in Example 7 was dissolved therein at a final concentration of 5% by weight to provide a mixed solution of hyaluronic acid-cinnamic acid ester and chondroitin sulfate-cinnamic acid ester. Using this solution, sheeting and irradiation were carried out by the procedures described in Example 1 to provide a crosslinked hyaluronic acid/ chondroitin sulfate film.

Similarly, a mixed solution containing HA-Cin-3 and CS-Cin-4 in a ratio of 2:1 or 1:2 (by weight) was prepared and the nonadhesive effect (to be described hereinafter) of each preparation was determined.

EXAMPLE 23

Synthesis of Heparin-cinnamic Acid Ester and Preparation of Crosslinked Heparin Film.

(1) Preparation of Heparin-cinnamic Acid Ester

To a solution of heparin tri-n-butylamine salt in DMF (500 mg/125 ml) was added 20 ml of pyridine and the mixture was dehydrated under reduced pressure. Then, with vigorous stirring at room temperature, 69.35 mg of cinnamoyl chloride was added. The reaction was carried out at 75° C. for 2 hours and the reaction mixture was then concentrated to 30 ml under reduced pressure at 40° C. To the residue was added ether and the resulting precipitate was recovered and dried under reduced pressure. The precipitate was dissolved in 5 ml of DMF and following addition of 40 ml of PBS, the solution was stirred well. The solution was dialyzed across a dyalysis membrane to thoroughly remove low molecular compounds and, then, lyophilized to provide 440 mg of the desired ester compound. Lot: Hep-Cin-1

The amount of bound cinnamic acid (determined by $^1$H-NMR), DS and solubility are shown in Table 7.

TABLE 7

| Lot | Bound cinnamic acid (wt. %) | DS | Solubility DMF | Water |
|---|---|---|---|---|
| Hep—Cin- 1 | 12.4 | 0.5 | o | Δ |
| 2 | 21.7 | 1.1 | o | x |
| 3 | 31.7 | 1.8 | o | x |
| 4 | 40.2 | 2.5 | o | x | o: Well soluble
Δ: Not well soluble but gel-like
x: Insoluble (2) Preparation of crosslinked heparin film In DMF was dissolved 30 mg of lot (Hep-Cin-1) and the solution was placed on a glass slide, 24 mm×24 mm, and dried with sterilized warm air at 40° C. The resulting film was irradiated with a 450 W high-pressure mercury lamp through a pyrex-covered water filter to provide a crosslinked heparin film. Lot: Hep-Cin-1-2

The contact angle (advancing and receding angles) and water swelling capacity are shown in Table 8.

TABLE 8

| Lot | Contact angle (°) advancing angle | receding angle | Water swelling capacity |
|---|---|---|---|
| Hep—Cin- 1-2 | 89.3 | 54.8 | 0.13 |
| 2-2 | 76.2 | 41.5 | 0.02 |
| 3-2 | 90.3 | 56.5 | 0.05 |

(3) Using the same materials and procedure as above, esters (Hep-Cin-2, Hep-Cin-3 and Hep-Cin-4) were prepared with the ratio of heparin to cynnamyl chloride varied (heparin fixed at 500 mg). The results of analysis are presented also in Table 7. Furthermore, crosslinked heparin films (Hep- Cin-2-2 and Hep-Cin-3-2) were prepared in the same manner. The physical properties of these films are shown also in Table 8.

EXAMPLE 24

A solution of hyaluronic acid tri-n-butylammonium salt (1.5 g corresponding to 10 mmol of OH groups) in dry DMF (200 ml) was kept under Argon atmosphere and cooled to 0° C. 4-Dimethylaminopyridine (0.305 g, 2.5 mmol), cinnamic anhydride (2.78 g, 10 mmol), and tri-n-butylamine (4.76 ml, 10 mmol) were successively added, and the reaction was allowed to proceed at room temperature for 24 hours. After cooling to 0° C., 5% $NaHCO_3$ in water (100 ml) was gradually added and the solution was stirred at room temperature for 48 hours. Excess $NaHCO_3$ was eliminated by progressive addition of 1M HCl to pH 4, and 1M NaOH to pH 7. Cold Ethanol was added under stirring. After decantation, the precipitate was dissolved in water, and the precipitation procedure was added under stirring. After decantation, the precipitate was dissolved in water, and the precipitation procedure was repeated with Ethanol. The precipitate was centrifuged off, dissolved in water, and passed through a column of Dowex 50(H+) cation-.exchange resin at 4° C. The acid was neutralized with 1M NaOH and lyophilized.

EXAMPLE 25

Nonadhesive Effect of Photocured (crosslinked) Hyaluronic Acid Film

A photocured hyaluronic acid-cinnamic acid ester film (DS=0.5; 30 μm thick, 20 mm×20 mm) as prepared in the same manner as the lot HA-Cin-3-2 prepared in Example 1 was used as the nonadhesive material and the following experiment was carried out.

The rat was laparotomized under anesthesia and the peritoneum parictale was mechanically injured to prepare a site of exposed muscle layer. The site was covered with the nonadhesive material prepared above. The implant was removed 1 week and 2 weeks after the coverage and the degree of tissue adhesion on the film surface was examined by light microscopy (after hematoxylin-eosin staining) and electron microscopy for evaluation. The rat in which the injured site was not covered was used as the control.

In the experiment using the nonadhesive materials of the invention} fibrin precipitation and cell adhesion were scarcely found in all samples after one week and two weeks. Findings after 2 weeks provided evidence that the biodegradation of the film had already begun.

On the other hand, in the control experiment, the injured site followed the sequence of fibrin precipitation, invasion of phlogocyte, fibroblasts, etc. and production of collagen and the intestinal canal had intimately adhered to the injured site by 1 week later.

The above experiment was repeated except that the crosslinked HA-Cin-3/CS-Cin-4 film prepared in Example 22 was used. Compared with the above homogeneous HA-Cin-3 film (HA-Cin-3-2), the biodegradability was enhanced so that the biodegradation of the film began within 1 week after implantation, accompanied by the invasion of cells into the film, and a progression of degradation was in evidence at 2 weeks.

EXAMPLE 26

Nonadhesive Effect of Photocured (crosslinked) Chondroitin Sulfate Film (in situ gelation)

The chondroitin sulfate-cinnamic acid ester lot CS-Cin-3 (DS=0.65) prepared in Example 7 was dissolved in phosphate buffer at a final concentration of 20% by weight to provide a nonadhesive material in the solution form.

An animal model of organ injury similar to that used in Example 25 was constructed and the injured site was coated with the above nonadhesive material. Then, this material was irradiated with UV light for 15 minutes to cause in situ gelation. Histological examination revealed a gel layer formed in intimate contact with the abdominal peritoneal tissue surface.

Serial observation of the injured site in the same manner as in Example 25 showed no adhesion just as in Example 25.

EXAMPLE 27

Nonadhesive Effect of Photocured (crosslinked) Hyaluronic Acid Film and Photocured (crosslinked) Chondroitin Sulfate Film The photocured hyaluronic acid-cinnamic acid ester (HA-Cin) films (DS=0.1, 0.5) prepared in the same manner as Examples 1 and 2 and the photocured hyaluronic acid-thymine derivative ester (HA-Thym; DS=0.2, 0.6, 0.9, 1.8) and the photocured chondroitin sulfate-thymine derivative ester (CS-Thym; DS=0.4, 0.9) films prepared in the same manner as Example 18 were used as the nonadhesive materials and the following experiment was carried out. Thus, each photocured film (14 mm dia.; 15–20 μm thick) was sterilized by immersing in 70% ethanol for 30 minutes and then kept afloat in sterilized water for 1 hour. As to samples of low DS, they were dried after immersing in water to remove the ethanol and before the animal experiment, immersed afloat in sterilized water for 10 minutes. The film absorbing water swelled to form a hydrogel.

A Wistar albino rat (male, 300 g) was anesthetized with ether and maintained with ether and oxygen till operation. One rat was used for each sample. A vertical midline incision was made in the rat abdomen to expose the liver. The surface of the exposed liver was mechanically injured to construct a damaged peritoneal site, 1 cm square, and the above swollen photocured film was applied. As to the film which could not be secured to the injured site, a plyurethane adhesive was spotted at the 4 corners to affix the film. Then, celiorrhaphy was performed with a nylon suture. One and 2 weeks after implantation, the rat was sacrificed and the sutured site was incised. The film covering the liver was macroscopically examined and the covered portion was excised together with the surrounding tissues and subjected to histological examination using a light microscope. The results are presented in Table 9.

TABLE 9

| Photo-crosslinked film | DS | Time after implantation | Adhesive | Macroscopic observation Adhesion | Microscopic observation Biodegradability | Film fracture |
|---|---|---|---|---|---|---|
| HA-Cin | 0.1 | 1 week | − | − | + | − |
| HA-Cin | 0.5 | 1 week | + | − | − | −, + |
| HA-Thym | 0.2 | 1 week | − | − | ++ | − |
| HA-Thym | 0.6 | 1 week | − | − | + | − |
| HA-Thym | 0.6 | 2 weeks | − | − | | |
| HA-Thym | 0.9 | 1 week | − | − | + | − |
| HA-Thym | 0.9 | 2 weeks | − | − | ++ | − |
| HA-Thym | 1.8 | 1 week | + | − | | |
| CS-Thym | 0.4 | 1 week | − | − | ++ | − |
| CS-Thym | 0.9 | 1 week | − | − | + | − |

−: None
+: Added or observed
++: Outstanding

Histological examination of the photocured HA-Cin (DS= 0.1) film, for instance, at 1 week after implantation revealed no cell adhesion on the film surface at all, with the biodegradation of the film having had begun and the invasion of the tissue being observed. In the case of the photocured HA-Thym (DS=0.2) film, flat cells like peritoneal cells were observed in the uppermost layer, with the biodegradation having had progressed and only the small central part remaining.

Using the uncovered site of injury as a control, a similar observation was made 1 week later. As a result, an adhesion which could not be separated by blunt procedures (e.g. operation with the back of an operating knife or a hand, not by cutting with a knife) was found between the injured surface of the liver and the abdominal wall.

EXAMPLE 28

Controlled Release of Drugs Utilizing Photocured (crosslinked) Hyaluronic Acid and Photocured (crosslinked) Chondroitin Sulfate Films as Carriers (1) Controlled Release of Indomethacin The HA-Thym having a varying IDS as obtained in Example 16 was dissolved in DMF at a final concentration of 5%, and 1 µg of indomethacin was dissolved in 200 µl of the above solution. The resulting solution was placed on a glass slide, 15 mm in diameter, and air-dried with sterilized warm air at 35° C. The film thus obtained was irradiated in the same manner as in Example 18 to provide an indomethacincontaining crosslinked hyaluronic acid film. The drug content was controlled at 10%. In the same manner, crosslinked hyaluronic acid films with 30%, 50% and 73% drug contents were prepared. Moreover, using the CS-Thym having a varying DS as obtained in Example 17, crosslinked chondroitin sulfate films with 10%, 30% and 50% drug contents were prepared in the same manner.

The test on release of the drug from each product film was performed as follows. Thus, the test film was suspended in water (20° C.) or phosphate-buffered saline (PBS) (37° C.) and stirred. The liquid phase was sampled at predetermined intervals of time and its ultraviolet absorption spectrum at 269 nm was measured.

Table 10 shows the relationship of the water dissolution test data for the photocured hyaluronic acid films (DS=0.7, 1.3, 1.8) having a drug content of 30% with DS and swelling capacity. As the dissolution test data, the time in which 20% of the drug was released from the film was used.

TABLE 10

| DS | Swelling capacity | 20% release time (min.) |
|---|---|---|
| 0.7 | 8 | 25 |
| 1.3 | 5 | 120 |
| 1.8 | 0.2 | 360 |

It is apparent from Table 10 that, as a tendency, the higher the DS, the higher is the degree of crosslinking and, hence, the harder is the film, with a consequent decrease in swelling capacity and an associated decrease in the rate of release of the drug. This finding suggested that the water-absorbing capacity of a film is an important factor in the rate of drug release. Regarding the films with DS values of 1.3 and 1.8, the rate of drug release tended to decrease with an increasing drug content.

The photocured hyaluronic acid films (DS=0.7, 2.2) and photocured chondroitin sulfate films (DS=0.8, 1.3, 1.8) were compared for the rates of drug release in PBS at drug contents of 10% and 50%. The results are shown in FIGS. 26 through 30. It will be apparent from these graphs that the controlled release of the drug is feasible with films having DS values not less than certain thresholds (for CS-Thym, DS=1.3).

(2) Controlled Release of Heparin

In a 20% aqueous solution of DMF was dissolved the chondroitin sulfate-cinnamic acid ester [CS-Cin-4 (DS= 1.37), CS-Cin-5 (DS=2.43)] obtained in Example 7 at a final concentration of 20% by weight as well as the hyaluronic acid-cinnamic: acid ester [HA-Cin-3(DS=0.50), HA-Cin-5 (DS=1.28), HA-Cin-6 (DS=2.43)] obtained in Examples 1 and 2 at a final concentration of 10% by weight. To 10 ml each of these solutions was added 100 mg of heparin and the solution was coated on a glass sheet (10cm×10 cm) and dried at room temperature for 1 hour to provide a film. This film was irradiated with a 450 W high-pressure mercury lamp for 30 minutes. The thickness of each film was approximately 100 µm.

Each of these films, as carried on the glass sheet, was completely submerged in a vessel containing 100 ml of water and stirred at 60 rpm. The amount of heparin released with time was determined by the carbazole-sulfuric acid method. The results showed that all the films provided for the controlled release of heparin.

Furthermore, each of the above controlled heparin releasing films was formed on the inner wall of a test tube. Then, in accordance with JP-A-4-41432, citrated blood was added and the clotting time was determined. All the samples showed antithrombotic activity.

(3) Controlled Release of Growth Hormone Releasing Factor

In a 20% aqueous solution of DMF was dissolved the hyaluronic acid-cinnamic acid ester (HA-Cin-3 (DS=0.50)] at a final concentration of 10% by weight and 1 mg of growth hormone releasing factor (GRF, human; mol. wt. 5039.8) was mixed into 1 ml of the above solution. The mixture was then coated on a glass sheet (3 cm×3 cm) and dried at room temperature for 1 hour to provide a film. This film was irradiated with a 450 W high-pressure mercury vapor lamp for 30 minutes. The thickness of this film was 110 µm.

The above film as carried on the glass sheet was completely submerged in a vessel containing 10 ml of water and stirred at 60 rpm. The GRF released with time was assayed by high performance liquid chromatography and the cumulative amount of release was calculated. It was found that the controlled release of GRF could be successfully implemented.

EXAMPLE 29

Vascular Prothesis

The inner surface of an artificial blood vessel with a small lumen (3 mm in inside diameter) was coated with a solution of the HA-Cin-3 obtained in Example 1 by the rotational coating technique and, after drying, the coated film cured with a UV irradiator utilizing a small caliber optical fiber, whereby a vascular prothesis internally coated with cured hyaluronic acid was obtained.

[Effects of the invention]

The present invention can readily provide readily purifiable photocurable GAGs by selecting, as highly safe and biocompatible starting materials, those photoreactive compounds and glycosaminoglycans specifically mentioned herein and binding the former to the latter. The invention can further provide materials for medical use by irradiating said photocurable GAGs with light. The materials have a two- or three-dimensional network structure and are highly safe, biocompatible and biodegradable/absorbable. The invention can further provide crosslinked GAG-based materials having desired physical characteristics required of materials for medical use by appropriately selecting the molecular weight of GAG, the DS of photoreactive compound, and other factors. Thus the invention is very widely applicable in various field of medicine.

While the invention has been described in detail and with reference to specific examples thereof, it will be apparent to one skilled in the art that various changes and modifications can be made therein without departing from the spirit and scope thereof.

What is claimed is:

1. A crosslinked glycosaminoglycan resistant to tissue and/or cell adhesion and biodegradable which is prepared by irradiating a photocurable glycosaminoglycan derivative with light to cause intermolecular and/or intramolecular crosslinking of photoreactive groups of the photocurable glycosaminoglycan derivative, wherein the photocurable glycosaminoglycan derivative is either (1) a photocurable glycosaminoglycan derivative which comprises a glycosaminoglycan and a photoreactive compound covalently bonded to said glycosaminoglycan, wherein said glycosaminoglycan is at least one member selected from the group consisting of hyaluronic acid, chondroitin, chondroitin sulfate, dermatan sulfate, heparin, heparan sulfate, keratosulfate, keratopolysulfate and derivatives thereof, said photoreactive compound is at least one member selected from the group consisting of substituted or unsubstituted cinnamic acids and reactive derivatives thereof, uracil derivatives having a carboxyalkyl group as a substituent in position 1 and reactive derivatives thereof, coumarin derivatives having a carboxyalkyl group as a substituent in position 7 and reactive derivatives thereof, and said photocurable glycosaminoglycan derivative is soluble in water and/or organic solvents and is curable by only irradiation with light;or (2) a photocurable glycosaminoglycan derivative which comprises a glycosaminoglycan and a photoreactive compound covalently bonded to said glycosaminoglycan and is represented by the formula:

gag—O—(CO—R¹);     [1]
gag—O—CO—R³—NH—CO—R¹;     [4c]
gag—CO—O—R³—O—CO—R¹;     [5c]
gag—CO—O—R³—NH—CO—R¹;     [5d]

gag—CO—NH—R³—O—CO—R¹;     [5e]

or gag—CO—NH—R³—NH—CO—R¹;     [5f]

wherein gag-O— and gag-CO— each is a residue of glycosaminoglycan which is at least one member selected from the group consisting of hyaluronic acid, chondroitin, chondroitin sulfate, dermatan sulfate, heparin, heparan sulfate, keratosulfate, keratopolysulfate and derivatives thereof, R³ —represents —(CH₂)ₙ—, wherein n is 1 to 10, —(CH₂)ₚCHY—, wherein Y is COOH or NH₂ and p is 1 to 10, or —(CH₂)ₘ—C₆H₄—(CH₂)ₗ—, wherein m is 1 to 10 and l is 1 to 10, and R¹—CO—is represented by the formula:

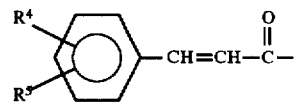

wherein R⁴ and R⁵ may be the same or different and each is a hydrogen atom, a lower alkyl, lower alkoxyl, nitro or amino group;

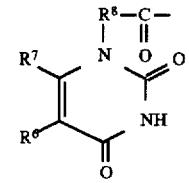

wherein R⁶ is a hydrogen or halogen atom or a lower alkyl or halo-lower alkyl group, R⁷ is a hydrogen or halogen atom or a cyano, carboxyl, lower alkoxycarbonyl, lower alkyl or halo-lower alkyl group, and R⁸ is a lower alkylene group; or

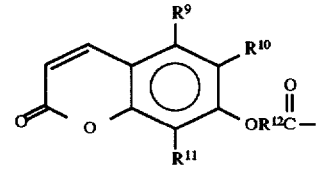

wherein R⁹, R¹⁰ and R¹¹ may be the same or different and each independently is a hydrogen atom or a lower alkyl group, and R¹² is a lower alkylene group, or said photocurable glycosaminoglycan derivative is represented by the formula:

gag—CO—(O—R¹);     [3]
gag—O—CO—R³—CO—O—R¹;     [4a]
gag—CO—O—R³—CO—O—R¹;     [5a]

or gag—CO—NH—R³—CO—O—R¹,     [5g]

wherein gag-O—, gag-CO— and R³ are as defined above and R¹—O— is represented by the formula:

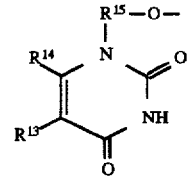

wherein R¹³ is a hydrogen atom or halogen atom or a lower alkyl or halo-lower alkyl group, R¹⁴ is a hydrogen or halogen atom or a cyano, carboxyl, lower alkoxycarbonyl, lower alkyl or halo-lower alkyl group, and R¹⁵ is a lower alkylene group; or

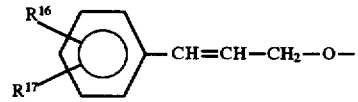

wherein R¹⁶ and R¹⁷ may be the same or different and each is a hydrogen atom, a lower alkyl, lower alkoxyl, nitro or amino group.

2. The crosslinked glycosaminoglycan according to claim 1, wherein said photocurable glycosaminoglycan derivative is molded and dried into a film, tubular or granular form.

3. The crosslinked glycosaminoglycan according to claim 2, which has a swelling capacity ranging from 0.1 to 200.

4. The crosslinked glycosaminoglycan according to claim 2, which has a contact angle with water ranging from 10° to 100°.

5. A crosslinked glycosaminoglycan-containing composition which comprises sterilized water and the crosslinked glycosaminoglycan of claim 2 immersed in said sterilized water.

6. The crosslinked glycosaminoglycan according to claim 1, wherein said photocurable glycosaminoglycan derivative is dissolved in a solvent selected from the group consisting of water, a buffer solution and an organic solvent of medically acceptable grade and the resulting solution sets to gel by irradiation with light.

7. A method of preventing cell and/or tissue adhesion which comprises applying to wound sites the crosslinked glycosaminoglycan of claim 1 comprising a glycosaminoglycan and a photoreactive compound covalently bonded thereto.

8. A method of producing a crosslinked glycosaminoglycan derivative resistant to tissue and/or cell adhesion and biodegradable which comprises dissolving a photocurable glycosaminoglycan derivative in a solvent selected from the group consisting of water, a buffer solution and an organic solvent of medically acceptable grade, molding it into a film, tubular or granular form, drying the resulting molded product to remove the solvent, and irradiating the product with light to cause intermolecular and/or intramolecular crosslinking of photoreactive groups of said photocurable glycosaminoglycan derivative, wherein the photocurable glycosaminoglycan derivative is a photocurable glycosaminoglycan derivative which comprises a glycosaminoglycan and a photoreactive compound covalently bonded to said glycosaminoglycan, wherein said glycosaminoglycan is at least one member selected from the group consisting of hyaluronic acid, chondroitin, chondroitin sulfate, dermatan sulfate, heparin, heparan sulfate, keratosulfate, keratopolysulfate and derivatives thereof, said photoreactive compound is at least one member selected from the group consisting of substituted or unsubstituted cinnamic acids and reactive derivatives thereof, uracil derivatives having a carboxyalkyl group as a substituent in position 1 and reactive derivatives thereof, coumarin derivatives having a carboxyalkyl group as a substituent in position 7 and reactive derivatives thereof, and said photocurable glycosaminoglycan derivative is soluble in water and/or organic solvents and is curable by only irradiation with light.

9. A composition comprising a crosslinked glycosaminoglycan resistant to tissue and/or cell adhesion and biodegradable which is prepared by irradiating a photocurable glycosaminoglycan derivative with light to cause intermolecular and/or intramolecular crosslinking of photoreactive groups of the photocurable glycosaminoglycan derivative, wherein the photocurable glycosaminoglycan derivative is either (1) a photocurable glycosaminoglycan derivative which comprises a glycosaminoglycan and a photoreactive compound covalently bonded to said glycosaminoglycan, wherein said glycosaminoglycan is at least one member selected from the group consisting of hyaluronic acid, chondroitin, chondroitin sulfate, dermatan sulfate, heparin, heparan sulfate, keratosulfate, keratopolysulfate and derivatives thereof, said photoreactive compound is at least one member selected from the group consisting of substituted or unsubstituted cinnamic acids and reactive derivatives thereof, uracil derivatives having a carboxyalkyl group as a substituent in position 1 and reactive derivatives thereof, coumarin derivatives having a carboxyalkyl group as a substituent in position 7 and reactive derivatives thereof, and said photocurable glycosaminoglycan derivative is soluble in water and/or organic solvents and is curable by only irradiation with lights; or (2) a photocurable glycosaminoglycan derivative which comprises a glycosaminoglycan and a photoreactive compound covalently bonded to said glycosaminoglycan and is represented by the formula:

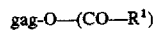

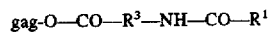

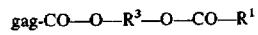

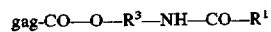

gag-CO—NH—R³—O—CO—R¹ or

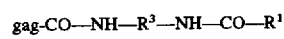

wherein gag-O— and gag-CO— each is a residue of glycosaminoglycan which is at least one member selected from the group consisting of hyaluronic acid, chondroitin, chondroitin sulfate, dermatan sulfate, heparin, heparan sulfate, keratosulfate, keratopolysulfate and derivatives thereof, $R^3$ represents —$(CH_2)_n$—, wherein n is 1 to 10, —$(CH_2)_p$,CHY—, wherein Y is COOH or $NH_2$ and p is 1 to 10, or —$(CH_2)_m$,—$C_6H_4$—$(CH_2)_l$—, wherein m is 1 to 10 and l is 1 to 10, and $R^1$—CO—is represented by the formula:

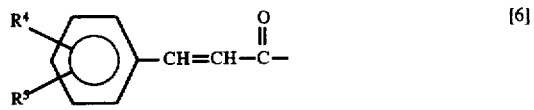

wherein $R^4$ and $R^5$ may be the same or different and each is a hydrogen atom, a lower alkyl, lower alkoxyl, nitro or amino group;

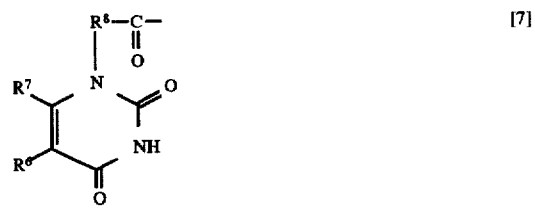

wherein $R^6$ is a hydrogen or halogen atom or a lower alkyl or halo-lower alkyl group, $R^7$ is a hydrogen or halogen atom or a cyano, carboxyl, lower alkoxycarbonyl, lower alkynyl or halo-lower alkyl group, and $R^8$ is a lower alkylene group; or

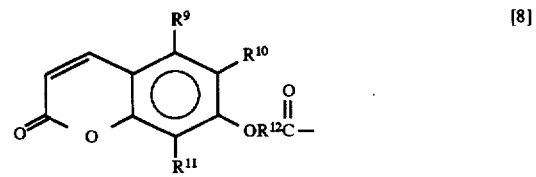

wherein $R^9$, $R^{10}$ and $R^{11}$ may be the same or different and each independently is a hydrogen atom or a lower alkyl group, and $R^{12}$ is a lower alkylene group; or said photocurable glycosaminoglycan derivative is represented by the formula:

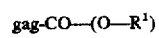

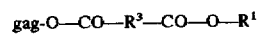

gag-CO—O—R³—CO—O—R¹ or gag-CO—NH—R³—CO—O—R¹ wherein gag-O—, gag-CO— and R³ are as defined above and R¹—O— is represented by the formula:

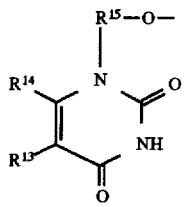   [9]

wherein R¹³ is a hydrogen atom or halogen atom or a lower alkyl or halo-lower alkyl group, R¹⁴ is a hydrogen or halogen atom or a cyano, carboxyl, lower alkoxycarbonyl, lower alkyl or halo-lower alkyl group, and R¹⁵ is a lower alkylene group; or

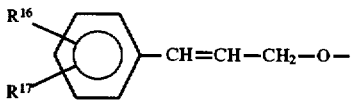   [10]

wherein R¹⁶ and R¹⁷ may be the same or different and each is a hydrogen atom, a lower alkyl, lower alkoxyl, nitro or amino group; and at least one component embedded therein or admixed therewith selected from the group consisting of organic solvents, water, buffer solutions, carriers, biological substances, drugs, physiologically active substances and pharmaceutically acceptable additives, which composition is formulated into films jellies, gels, suspensions, microcapsules, tablets, granules, or powders.

10. The composition of claim 9 in which the photocurable glycosaminoglycan derivative is represented by the formula:

gag-O—(CO—R¹)

gag-CO—NH—R³—O—CO—R¹ or gag-CO—NH—R³—NH—CO—R¹ wherein gag-O—and gag-CO—each is a residue of hyaluronic acid or chondroitin sulfate, R³ represents —(CH₂)ₙ—, wherein n is 1 to 10, —(CH₂)ₚCHY—, wherein Y is COOH or NH₂ and p is 1 to 10, or —(CH₂)ₘ—C₆H₄—(CH₂)ᵣ—, wherein m is 1 to 10 and l is 1 to 10, and R¹—CO—is represented by the formula:

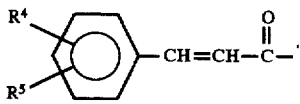   [6]

wherein R⁴ and R⁵ may be the same or different and each is a hydrogen atom, a lower alkyl, lower alkoxyl, nitro or amino group;

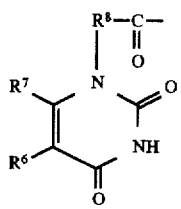   [7]

wherein R⁶ is a hydrogen or halogen atom or a lower alkyl or halo-lower alkyl group, R⁷ is a hydrogen or halogen atom or a cyano, carboxyl, lower alkoxycarbonyl, lower alkyl or halo-lower alkyl group, and R⁸ is a lower alkylene group.

11. The composition of claim 9 which is in the form of film, jellies or gels and has physicochemical properties and/or shape effective for preventing tissue adhesion.

12. The composition of claim 11 which is sterilized and absorbing water swelled to form a hydrogel.

13. A crosslinked glycosaminoglycan resistant to tissue and/or cell adhesion and biodegradable which is prepared by irradiating a photocurable glycosaminoglycan derivative with light to cause intermolecular and/or intramolecular crosslinking of photoreactive groups of the photocurable glycosaminoglycan derivative, wherein the photocurable glycosaminoglycan derivative is a photocurable glycosaminoglycan derivative which comprises a glycosaminoglycan and a photoreactive compound covalently bonded to said glycosaminoglycan, wherein said glycosaminoglycan is at least one member selected from the group consisting of hyaluronic acid, chondroitin, chondroitin sulfate, dermatan sulfate, heparin, heparan sulfate, keratosulfate, keratopolysulfate and derivatives thereof, said photoreactive compound has at least one member selected from the group consisting of the groups represented by the formulae:

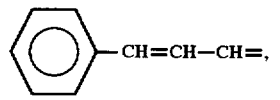

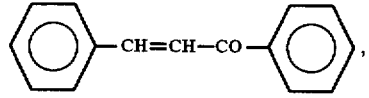

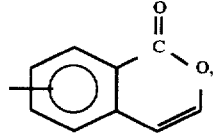

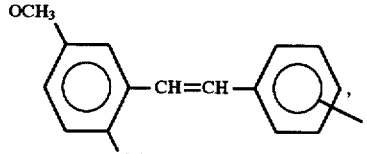

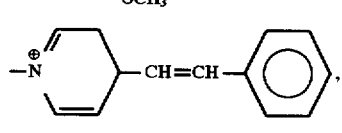

41
-continued
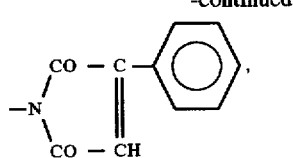
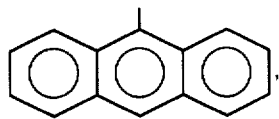
42
-continued
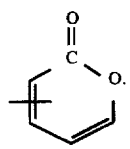
* * * * *

UNITED STATES PATENT AND TRADEMARK OFFICE
CERTIFICATE OF CORRECTION

PATENT NO. : 5,763,504
DATED : June 9, 1998
INVENTOR(S) : MATSUDA et al.

It is certified that error appears in the above-identified patent and that said Letters Patent is hereby corrected as shown below:

On the title page;

At item [62] in the cover page, the description "Division of Ser. No. 13,799, Feb. 5, 1993, abandoned" should correctly read --Division of Ser. No. 13,799, Feb. 5, 1993, U.S. Patent No. 5,462,976--.

Signed and Sealed this

Ninth Day of February, 1999

Attest:

Attesting Officer

*Acting Commissioner of Patents and Trademarks*